(12) United States Patent
Ebbinghaus et al.

(10) Patent No.: US 7,405,041 B2
(45) Date of Patent: Jul. 29, 2008

(54) METHODS FOR REGULATING TRANSCRIPTION BY TARGETING QUADRUPLEX DNA

(75) Inventors: Scot W. Ebbinghaus, Tucson, AZ (US); Laurence H. Hurley, Tucson, AZ (US); Adam Siddiqui-Jain, San Diego, CA (US); Regan Memmott, Tucson, AZ (US)

(73) Assignee: Arizona Board of Regents on behalf of the University of Arizona, Tuscon, AZ (US)

( * ) Notice: Subject to any disclaimer, the term of this patent is extended or adjusted under 35 U.S.C. 154(b) by 323 days.

(21) Appl. No.: 10/645,471

(22) Filed: Aug. 20, 2003

(65) Prior Publication Data

US 2004/0171022 A1 Sep. 2, 2004

Related U.S. Application Data

(60) Provisional application No. 60/404,965, filed on Aug. 20, 2002.

(51) Int. Cl.
*C12Q 1/68* (2006.01)
(52) U.S. Cl. .......................................... 435/6
(58) Field of Classification Search ........................ None
See application file for complete search history.

(56) References Cited

U.S. PATENT DOCUMENTS

| 5,176,996 | A  |   | 1/1993  | Hogan et al. |
| 6,156,763 | A  |   | 12/2000 | Kerwin et al. ................ 514/279 |
| 6,544,784 | B1 | * | 4/2003  | Bullerdiek et al. ........... 435/325 |
| 2002/0115057 | A1 | * | 8/2002  | Young ............................ 435/4 |
| 2003/0207834 | A1 | * | 11/2003 | Dale et al. ..................... 514/44 |
| 2004/0005601 | A1 | * | 1/2004  | Siddiqui-Jain et al. ......... 435/6 |

OTHER PUBLICATIONS

Izbicka et al. Telomere-interactive agents affect proliferation rates and induce chromosomal destabilization in sea urchin embryos. Anti-Cancer Drug Desgin. (1999) 14: 355-365.*
Lee. The stability of polypurine tetraplexes in the presence of mono- and divalent cations. Nucleic Acids Research. (1990) 18(20): 6057-6060.*
Williams et al. Advantages of firefly luciferase as a reporter gene: application to the interleukin-2 gene promoter, Analytical Biochemistry. (1989) 176: 28-32.*
Benson et al. GenBank. Nucleic Acids Research (2000) 28(1): 15-18.*
GenBank® GI: 927059, Apr. 9, 1996 [online], [retrieved on Jun. 4, 2007], retrieved from the Internet: <URL: www.ncbi.nlm.nih.gov/entrez/viewer.fcgi?db=nuccore&id=927059).*
Anantha et al., Biochemistry 37(9):2709-2714 (1998).
Cohen et al., J Biol Chem 72:2901-2913 (1997).
Datta et al., JACS 123:9612-9619 (2001).
Ewulonu et al., Proc Natl Acad Sci 88:4675 (1991).
Han et al., Nucl. Acids Res. 27:537-542 (1999).
He et al., Science 281:1509-1512 (1998).
Hurley et al., Pharmacology & Therapeutics 85:141-158 (2000).
Hurley, Nature Rev. Cancer 2:188-200 (2002).
Jin & Pike, Mol. Endocrinol. 10:196-205 (1996).
Marathias and Bolton, Biochemistry 38:4355-4364 (1999).
Matsugami et al., J. Mol. Biol. 313:255-269 (2001).
Matsugami et al., J. Biol. Chem. 278(30):28147-28153 (2003).
Postel et al., Mol. Cell. Biol. 9:5123-5133 (1989).
Postel, J. Biol. Chem. 274:22821-22829 (1999).
Ren et al., Biochemistry 38:16067-16075 (1999).
Rustighi et al., Biochem. Biophys. Res. Comm. 265:439-447 (1999).
Rustighi et al., Biochemistry 41:1229-1240 (2002).
Shin-ya et al., J. Am. Chem. Soc. 123:1262 (2001).
Simonsson et al., Nucleic Acids Research 26(5):1167-1172 (1998).
Tone et al., J Immunology 165:286-91 (2000).
Weitzmann et al., J. Biol. Chem. 271:20958-20964 (1996).
Invitation to Pay Additional Fees for PCT/US03/26267 mailed on Sep. 16, 2004, 2 pages.
Gowan et al., Molecular Pharmacology (2002) 61:1154-1162.
International Search Report for PCT/US03/26267, mailed on Dec. 8, 2004, 5 pages.
Mergny et al., Anti-Cancer Drug Design (1999) 14:327-339.
Armitage Group, the, "Hybridization of Peptide Nucleic Acid Probes to Structured DNA and RNA Targets" at <http://www.chem.cme.edu/groups/army/research/probes.html> (Visited May 15, 2003).
Arthanari et al., Chemistry and Biology (2001) 8:221-230.
Arthanari et al., Anti-Cancer Drug Design (1999) 14:317-326.
Cooney et al., Science (1988) 241:456-459.
Doyle et al., "Inhibition of Gene Expression Inside Cells by Peptide Nucleic Acids: Effect of mRNA Target Sequence, Mismatched Bases, and PNA Length" Biochemistry 40:53-64 (2001).
Finkenzeller et al., "Sp1 Recognition Sites in the Proximal Promoter of the Human Vascular Endothelial Growth Factor Gene are Essential for Platelet-Derived Growth Factor-Induced Gene Expression" Oncogene 15:669-676 (1997).
Grand et al., PNAS USA (2004) 101(16):6140-6145.
Han et al., J. Am. Chem. Soc. 121:3561-3570 (1999).
Hans et al., TIBS (2000) 21:136-140.
Hurley et al., Abstracts of the American Chemical Society (2000) abstract PHYS-262 (abstract only).
International Search Report for PCT/US03/10658, mailed on Dec. 3, 2004, 6 pages.

(Continued)

*Primary Examiner*—Kenneth R. Horlick
*Assistant Examiner*—Angela Bertagna
(74) *Attorney, Agent, or Firm*—Morrison & Foerster LLP

(57) ABSTRACT

Among the different intrastrand quadruplex structures that can arise from duplex DNA, it has been discovered that the nucleotide sequences $(GGA)_4$ (SEQ ID NO: 1) and (GGA) $_3$GG (SEQ ID NO: 2) form biologically significant quadruplex structures. Thus, provided herein are methods for identifying molecules that modulate the biological activity of quadruplex DNA comprising the nucleotide sequence $(GGA)_4$ (SEQ ID NO: 1) or the nucleotide sequence (GGA) $_3$GG (SEQ ID NO: 2), and specifically, methods for identifying molecules that bind such quadruplexes. Also provided herein are methods for modulating the biological activity of a biologically significant native quadruplex DNA with a molecule identified by the methods described herein.

6 Claims, 2 Drawing Sheets

OTHER PUBLICATIONS

Invitation to Pay Additional Fees for PCT/US03/10658, mailed on Aug. 24, 2004, 2 pages.
Jing et al., J. Biomol. Struct. Dyn. 15:573-585 (1997).
Jing et al., J. Biol. Chem. 273:34992-34999 (1998).
Kelly et al., J. Mol. Biol. 256:417-422 (1996).
Kettani et al., "A Two-Stranded Template-Based Approach to G (C-A) Triad Formation: Designing Novel Structural Elements into an Existing DNA Framework" J. Mol. Biol. 301:129-146 (2000).
Kim et al. Biochemistry (1998) 37:2299-2304.
Kuryavyi et al., "A Diamond-Shaped Zipper-like DNA Architecture Containing Triads Sandwiched between Mismatches and Tetrads" J. Mol. Biol. 295:455-469 (2000).
Kuryavyi et al., "A Double Chain Reversal Loop and Two Diagonal Loops Define the Architecture of a Unimolecular DNA Quadruplex Containing a Pair of Stacked G(syn) G(syn) G(anti) G(anti) Tetrads Flanked by a G (T-T) Triad and a T T T Triple" J. Mol. Biol. 310:181-194 (2001).
Lew et al., Proc. Natl. Acad. Sci. USA 97:12508-12512 (2000).
Li et al., Nucleic Acids Research (2005) 33(14):4649-4659.
Ma et al., "NM23-H1 and NM23-H2 Repress Transcriptional Activities of Nuclease-Hypersensitive Elements in the Platelet-Derived Growth Factor-A Promoter" J. Biol. Chem. 277(2):1560-1567 (2002).
Phan et al., Journal of the American Chemical Society (2004) 126(28):8710-8716.
Phan et al., Nature Chemical Biology (2005) 1(3):167-173.
Postel et al., J. Bioenerg. Biomembr. 32:277-284 (2000).
Rangan et al., J. Biol. Chem. (2001) 276(7):4640-4646.
Schultze et al., J. Mol. Biol. 235:1532-1547 (1994).
Seenisamy et al., Journal of the American Chemical Society (2004) 126(28):8702-8709.
Siddiqui-Jain et al.. PNAS USA (2002) 99(18):11593-11598.
Simonsson et al., J. Biol. Chem. (1999) 274(24):17379-17383.
Simonsson et al., Biochem. Biophys. Res. Comm. (2002) 290:11-15.
Sun et al., "Inhibition of Human Telomerase by a G-Quadruplex-Interactive Compound" J. Med. Chem. 40:2113-2116 (1997).
Supplementary European Search Report for EP 03 74 6640, mailed on Jun. 24, 2005, 3 pages.
Written Opinion for PCT/US03/10658, mailed on May 16, 2005, 6 pages.
Preliminary Amendment from U.S. Appl. No. 10/407,449, filed on Apr. 8, 2004.
Restriction Requirement from U.S. Appl. No. 10/407,449, mailed on Oct. 21, 2005.
Amendment in Response to Non-Final Office Action from U.S. Appl. No. 10/407,449, filed on Nov. 21, 2005.
Non-Final Office Action from U.S. Appl. No. 10/407,449, mailed on Dec. 20, 2005.
Amendment in Response to Non-Final Office Action from U.S. Appl. No. 10/407,449, filed on Jun. 20, 2006.
Final Office Action from U.S. Appl. No. 10/407,449, mailed on Jul. 14, 2006.
Preliminary Amendment and RCE from U.S. Appl. No. 10/407,449, filed on Dec. 1, 2006.
Non-Final Office Action from U.S. Appl. No. 10/407,449, mailed on Jan. 30, 2007.
Amendment in Response to Non-Final Office Action from U.S. Appl. No. 10/407,449, filed on Jul. 30, 2007.

* cited by examiner

FIGURE 2

5'TTTCTCAGGAGAAAGAGCagCagCagCTCACGGAGG
AGGAGGAGAAGGAGGAGAAACAGGTT3'

Region I: CagCagCagC
Region II: TCACGGAGG
Region III: AGGAGGAGAAGGAGGAGA

Sequence of c-myb 66 with G-C Mutations of Region 1

SEQUENCE LISTING

```
<160> NUMBER OF SEQ ID NOS: 32

<210> SEQ ID NO 1
<211> LENGTH: 12
<212> TYPE: DNA
<213> ORGANISM: Unknown
<220> FEATURE:
<223> OTHER INFORMATION: oligonucleotide

<400> SEQUENCE: 1
ggaggaggag ga                                                         12

<210> SEQ ID NO 2
<211> LENGTH: 11
<212> TYPE: DNA
<213> ORGANISM: Unknown
<220> FEATURE:
<223> OTHER INFORMATION: oligonucleotide

<400> SEQUENCE: 2
ggaggaggag g                                                          11

<210> SEQ ID NO 3
<211> LENGTH: 22
<212> TYPE: DNA
<213> ORGANISM: Unknown
<220> FEATURE:
<223> OTHER INFORMATION: oligonucleotide

<400> SEQUENCE: 3
ggaggaggag gggaggagga gg                                              22

<210> SEQ ID NO 4
<211> LENGTH: 23
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: 12
<223> OTHER INFORMATION: n = A,T,C or G

<400> SEQUENCE: 4
ggaggaggag gnggaggagg agg                                             23

<210> SEQ ID NO 5
<211> LENGTH: 24
<212> TYPE: DNA
<213> ORGANISM: Unknown
<220> FEATURE:
<223> OTHER INFORMATION: oligonucleotide
```

```
<220> FEATURE:
<221> NAME/KEY: misc_feature
<222> LOCATION: 12, 13
<223> OTHER INFORMATION: n = A,T,C or G

<400> SEQUENCE: 5
ggaggaggag gnnggaggag gagg                                                24

<210> SEQ ID NO 6
<211> LENGTH: 25
<212> TYPE: DNA
<213> ORGANISM: Unknown
<220> FEATURE:
<223> OTHER INFORMATION: oligonucleotide
<220> FEATURE:
<221> NAME/KEY: misc_feature
<222> LOCATION: 12, 13, 14
<223> OTHER INFORMATION: n = A,T,C or G

<400> SEQUENCE: 6
ggaggaggag gnnnggagga ggagg                                               25

<210> SEQ ID NO 7
<211> LENGTH: 26
<212> TYPE: DNA
<213> ORGANISM: Unknown
<220> FEATURE:
<223> OTHER INFORMATION: oligonucleotide
<220> FEATURE:
<221> NAME/KEY: misc_feature
<222> LOCATION: 12, 13, 14, 15
<223> OTHER INFORMATION: n = A,T,C or G

<400> SEQUENCE: 7
ggaggaggag gnnnnggagg aggagg                                              26

<210> SEQ ID NO 8
<211> LENGTH: 27
<212> TYPE: DNA
<213> ORGANISM: Unknown
<220> FEATURE:
<223> OTHER INFORMATION: oligonucleotide
<220> FEATURE:
<221> NAME/KEY: misc_feature
<222> LOCATION: 12, 13, 14, 15, 16
<223> OTHER INFORMATION: n = A,T,C or G

<400> SEQUENCE: 8
ggaggaggag gnnnnnggag gaggagg                                             27

<210> SEQ ID NO 9
<211> LENGTH: 28
<212> TYPE: DNA
<213> ORGANISM: Unknown
<220> FEATURE:
<223> OTHER INFORMATION: oligonucleotide
<220> FEATURE:
<221> NAME/KEY: misc_feature
<222> LOCATION: 12, 13, 14, 15, 16, 17
<223> OTHER INFORMATION: n = A,T,C or G

<400> SEQUENCE: 9
ggaggaggag gnnnnnngga ggaggagg                                            28

<210> SEQ ID NO 10
<211> LENGTH: 29
<212> TYPE: DNA
<213> ORGANISM: Unknown
<220> FEATURE:
```

```
<223> OTHER INFORMATION: oligonucleotide
<220> FEATURE:
<221> NAME/KEY: misc_feature
<222> LOCATION: 12, 13, 14, 15, 16, 17, 18
<223> OTHER INFORMATION: n = A,T,C or G

<400> SEQUENCE: 10
ggaggaggag gnnnnnnngg aggaggagg                                    29

<210> SEQ ID NO 11
<211> LENGTH: 30
<212> TYPE: DNA
<213> ORGANISM: Unknown
<220> FEATURE:
<223> OTHER INFORMATION: oligonucleotide
<220> FEATURE:
<221> NAME/KEY: misc_feature
<222> LOCATION: 12, 13, 14, 15, 16, 17, 18, 19
<223> OTHER INFORMATION: n = A,T,C or G

<400> SEQUENCE: 11
ggaggaggag gnnnnnnnng gaggaggagg                                   30

<210> SEQ ID NO 12
<211> LENGTH: 31
<212> TYPE: DNA
<213> ORGANISM: Unknown
<220> FEATURE:
<223> OTHER INFORMATION: oligonucleotide
<220> FEATURE:
<221> NAME/KEY: misc_feature
<222> LOCATION: 12, 13, 14, 15, 16, 17, 18, 19, 20
<223> OTHER INFORMATION: n = A,T,C or G

<400> SEQUENCE: 12
ggaggaggag gnnnnnnnnn ggaggaggag g                                 31

<210> SEQ ID NO 13
<211> LENGTH: 32
<212> TYPE: DNA
<213> ORGANISM: Unknown
<220> FEATURE:
<223> OTHER INFORMATION: oligonucleotide
<220> FEATURE:
<221> NAME/KEY: misc_feature
<222> LOCATION: 12, 13, 14, 15, 16, 17, 18, 19, 20, 21
<223> OTHER INFORMATION: n = A,T,C or G

<400> SEQUENCE: 13
ggaggaggag gnnnnnnnnn nggaggagga gg                                32

<210> SEQ ID NO 14
<211> LENGTH: 66
<212> TYPE: DNA
<213> ORGANISM: Unknown
<220> FEATURE:
<223> OTHER INFORMATION: oligonucleotide

<400> SEQUENCE: 14
tttctcagga gaaagagcag cagcagctca cggaggagga ggagaaggag gaggaggaaa  60
caggtt                                                             66

<210> SEQ ID NO 15
<211> LENGTH: 27
<212> TYPE: DNA
<213> ORGANISM: Unknown
<220> FEATURE:
<223> OTHER INFORMATION: oligonucleotide
```

<400> SEQUENCE: 15
ggaggaggag gaagaggagg aggaggc                                   27

<210> SEQ ID NO 16
<211> LENGTH: 38
<212> TYPE: DNA
<213> ORGANISM: Unknown
<220> FEATURE:
<223> OTHER INFORMATION: oligonucleotide

<400> SEQUENCE: 16
agagaagagg ggaggaggag gaggagagga ggaggcgc                       38

<210> SEQ ID NO 17
<211> LENGTH: 13
<212> TYPE: DNA
<213> ORGANISM: Unknown
<220> FEATURE:
<223> OTHER INFORMATION: oligonucleotide

<400> SEQUENCE: 17 ggaggggag ggg                                                   13

<210> SEQ ID NO 18
<211> LENGTH: 28
<212> TYPE: DNA
<213> ORGANISM: Unknown
<220> FEATURE:
<223> OTHER INFORMATION: oligonucleotide

<400> SEQUENCE: 18
aggagaagga ggaggtggag gaggaggg                                  28

<210> SEQ ID NO 19
<211> LENGTH: 32
<212> TYPE: DNA
<213> ORGANISM: Unknown
<220> FEATURE:
<223> OTHER INFORMATION: oligonucleotide

<400> SEQUENCE: 19
ggaggaggaa gaatgcgagg aggagggagg ag                             32

<210> SEQ ID NO 20
<211> LENGTH: 25
<212> TYPE: DNA
<213> ORGANISM: Unknown
<220> FEATURE:
<223> OTHER INFORMATION: oligonucleotide

<400> SEQUENCE: 20
ccgaaggagg aaggaggagg agggg                                     25

<210> SEQ ID NO 21
<211> LENGTH: 35
<212> TYPE: DNA
<213> ORGANISM: Unknown
<220> FEATURE:
<223> OTHER INFORMATION: oligonucleotide

<400> SEQUENCE: 21
agcgaggagg aggaggagga ggaggaggag aggaa                          35

<210> SEQ ID NO 22

```
<211> LENGTH: 17
<212> TYPE: DNA
<213> ORGANISM: Unknown
<220> FEATURE:
<223> OTHER INFORMATION: oligonucleotide

<400> SEQUENCE: 22
agaagaggga ggaggag                                                   17

<210> SEQ ID NO 23
<211> LENGTH: 13
<212> TYPE: DNA
<213> ORGANISM: Unknown
<220> FEATURE:
<223> OTHER INFORMATION: oligonucleotide

<400> SEQUENCE: 23
ggaaggagga gga                                                       13

<210> SEQ ID NO 24
<211> LENGTH: 21
<212> TYPE: DNA
<213> ORGANISM: Unknown
<220> FEATURE:
<223> OTHER INFORMATION: oligonucleotide

<400> SEQUENCE: 24
ctcctcctcc ttcccctccc c                                              21

<210> SEQ ID NO 25
<211> LENGTH: 16
<212> TYPE: DNA
<213> ORGANISM: Unknown
<220> FEATURE:
<223> OTHER INFORMATION: oligonucleotide

<400> SEQUENCE: 25
ggaggaccga ggagga                                                    16

<210> SEQ ID NO 26
<211> LENGTH: 16
<212> TYPE: DNA
<213> ORGANISM: Unknown
<220> FEATURE:
<223> OTHER INFORMATION: oligonucleotide

<400> SEQUENCE: 26
cctcctggct cctcct                                                    16

<210> SEQ ID NO 27
<211> LENGTH: 15
<212> TYPE: DNA
<213> ORGANISM: Unknown
<220> FEATURE:
<223> OTHER INFORMATION: oligonucleotide

<400> SEQUENCE: 27
tccaactatg tatac                                                     15

<210> SEQ ID NO 28
<211> LENGTH: 35
<212> TYPE: DNA
<213> ORGANISM: Unknown
<220> FEATURE:
<223> OTHER INFORMATION: oligonucleotide

<400> SEQUENCE: 28
```

```
<210> SEQ ID NO 29
<211> LENGTH: 36
<212> TYPE: DNA
<213> ORGANISM: Unknown
<220> FEATURE:
<223> OTHER INFORMATION: oligonucleotide

<400> SEQUENCE: 29
tcacaggaga aggaggaggt ggaggaggag ggctgc                            36

<210> SEQ ID NO 30
<211> LENGTH: 86
<212> TYPE: DNA
<213> ORGANISM: Unknown
<220> FEATURE:
<223> OTHER INFORMATION: oligonucleotide

<400> SEQUENCE: 30
tccaactatg tatactcaca ggagaaggag gaggtggagg aggagggctg cttagcggca   60
cgcaattgct atagtgagtc gtatta                                       86

<210> SEQ ID NO 31
<211> LENGTH: 75
<212> TYPE: DNA
<213> ORGANISM: Unknown
<220> FEATURE:
<223> OTHER INFORMATION: oligonucleotide

<400> SEQUENCE: 31
tttctcagga gaaagaggag gaggaggagg tcacggagga ggaggaggag aaggaggagg   60
aggaggaaac aggtt                                                   75

<210> SEQ ID NO 32
<211> LENGTH: 120
<212> TYPE: DNA
<213> ORGANISM: Unknown
<220> FEATURE:
<223> OTHER INFORMATION: oligonucleotide

<400> SEQUENCE: 32
tccaactatg tatactttct caggagaaag aggaggagga ggaggtcacg gaggaggagg   60
aggagaagga ggaggaggag gaaacaggtt ttagcgacat tgctatagtg agtcgtatta  120
```
ttagcgacac gcaattgcta tagtgagtcg tatta 35

METHODS FOR REGULATING TRANSCRIPTION BY TARGETING QUADRUPLEX DNA

CROSS-REFERENCE TO RELATED APPLICATIONS

This application claims benefit of U.S. application Ser. No. 60/404,965, filed Aug. 20, 2002. The content of that application is incorporated herein by reference in its entirety.

STATEMENT REGARDING FEDERALLY SPONSORED RESEARCH

This invention was made in part with government support under Grant Nos. CA67760, CA88310, CA76568 and CA85306 awarded by the National Institutes of Health. The government has certain rights in this invention.

FIELD OF THE INVENTION

This invention relates to DNA sequences capable of forming a particular class of secondary structure referred to as a quadruplex.

BACKGROUND

Developments in molecular biology have led to an understanding of how certain therapeutic compounds interact with molecular targets and lead to a modified physiological condition. Specificity of therapeutic compounds for their targets is derived in part from interactions between complementary structural elements in the target molecule and the therapeutic compound. A greater variety of target structural elements in the target leads to the possibility of unique and specific target/compound interactions. Because polypeptides are structurally diverse, researchers have focused on this class of targets for the design of specific therapeutic molecules.

In addition to therapeutic compounds that target polypeptides, researchers also have identified compounds that target DNA. Some of these compounds are effective anticancer agents and have led to significant increases in the survival of cancer patients. Unfortunately, however, these DNA targeting compounds do not act specifically on cancer cells and therefore are extremely toxic. Their unspecific action may be due to the fact that DNA often requires the uniformity of Watson-Crick duplex structures for compactly storing information within the human genome. This uniformity of DNA structure does not offer a structurally diverse population of DNA molecules that can be specifically targeted.

Nevertheless, there are some exceptions to this structural uniformity, as certain DNA sequences can form unique secondary structures. For example, intermittent runs of guanines can form G-quadruplex structures, and complementary runs of cytosines can form i-motif structures. Formation of G-quadruplex and i-motif structures occurs when a particular region of duplex DNA transitions from Watson-Crick base pairing to intermolecular and intramolecular single-stranded structures.

SUMMARY

Certain regulatory regions in duplex DNA can transition into single stranded structures, including intrastrand quadruplex structures. These regulatory regions can form different intramolecular quadruplex conformations. One is a basket conformation, where the bridging loop runs diagonal to the two parallel loops. Another, which can be kinetically facile, is a chair conformation where the bridging loops run orthogonal to the two parallel loops and is a folded-over hairpin (see e.g., U.S. patent application Ser. No. 10/407,449 filed Apr. 4, 2003). Still another is a quadruplex conformation identified herein, which is present in transcription regulatory regions comprising the nucleotide sequence $(GGA)_4$ (SEQ ID NO:1) or the nucleotide sequence $(GGA)_3GG$ (SEQ ID NO:2). It has been discovered that quadruplex DNA comprising these nucleotide sequences is biologically significant in that it regulates transcription of certain oncogenes, such as HER-2/neu and c-MYB. Identifying this biologically significant quadruplex conformation paves the way for identifying molecules that specifically interact with quadruplex structures.

Thus, featured herein is a method for identifying a molecule that modulates the biological activity of a native quadruplex nucleic acid, which comprises contacting a test quadruplex nucleic acid comprising the nucleotide sequence $(GGA)_4$ (SEQ ID NO:1) or the nucleotide sequence $(GGA)_3GG$ (SEQ ID NO:2) with a candidate molecule, and determining the presence or absence of an interaction between the candidate molecule and the test quadruplex nucleic acid. One embodiment is a method for identifying a molecule that binds to quadruplex nucleic acid, which comprises contacting a test quadruplex nucleic acid with a candidate molecule, where the quadruplex nucleic acid comprises the nucleotide sequence $(GGA)_4$ (SEQ ID NO:1) or the nucleotide sequence $(GGA)_3GG$ (SEQ ID NO:2), and determining the presence or absence of binding between the candidate and the test quadruplex nucleic acid.

Also featured is a method for modulating the biological activity of a biologically significant quadruplex nucleic acid comprising the nucleotide sequence $(GGA)_4$ (SEQ ID NO:1) or the nucleotide sequence $(GGA)_3GG$ (SEQ ID NO:2), which comprises contacting a system comprising quadruplex nucleic acid, such as native quadruplex nucleic acid, with a molecule which interacts with the quadruplex nucleic acid.

Another feature is a method for identifying a sequence capable of forming an intramolecular quadruplex monomer or intramolecular quadruplex dimer, which comprises contacting a nucleic acid having the nucleotide sequence $(GGA)_4$ (SEQ ID NO:1) or the nucleotide sequence $(GGA)_3GG$ (SEQ ID NO:2) with a compound that binds to an iintramolecular quadruplex monomer and/or intramolecular quadruplex dimer, wherein the intramolecular quadruplex is a tetrad stabilized by a second planar structure in a parallel orientation to the tetrad, whereby the intramolecular quadruplex monomer or intramolecular quadruplex dimer is identified. In specific embodiments, the compound is TMPyP4 and/or telomestatin.

In specific embodiments of the methods described above, the nucleic acid is DNA, and includes the nucleotide sequence $(GGA)_3GGX_n(GGA)_3GG$, where n is 0, 1, 2, 3, 4 or 5-10 (SEQ ID NOS:3-13). In other embodiments, the nucleic acid consists of the nucleotide sequence $(GGA)_4$ (SEQ ID NO:1), $(GGA)_3GG$ (SEQ ID NO:2) or $(GGA)_3GGX_n(GGA)_3GG$, where n is n is 0, 1, 2, 3, 4 or 5-10 (SEQ ID NOS:3-13). In an embodiment, the nucleic acid is capable of forming an intramolecular heptad/tetrad quadruplex monomer or an intramolecular heptad/tetrad quadruplex dimer.

Also featured herein is a method for identifying native nucleotide sequences capable of forming a quadruplex structure that modulates a biological activity, which comprises searching a database comprising nucleotide sequence information for those that include the subsequence $(GGA)_4$ (SEQ ID NO:1), the subsequence $(GGA)_3GG$ (SEQ ID NO:2), or the subsequence $(GGA)_3GGX_n(GGA)_3GG$, where n is an integer between 1 and 3 (SEQ ID NOS:4-6), and identifying a subset of the nucleotide sequences in the database comprising one of these subsequences located adjacent to an end of an open reading frame of a gene.

BRIEF DESCRIPTION OF THE DRAWINGS

FIG. 2 (SEQ ID NO:14) shows nucleotide moieties in a c-MYB nucleotide sequence that have been mutated.

DETAILED DESCRIPTION

Figure 1:
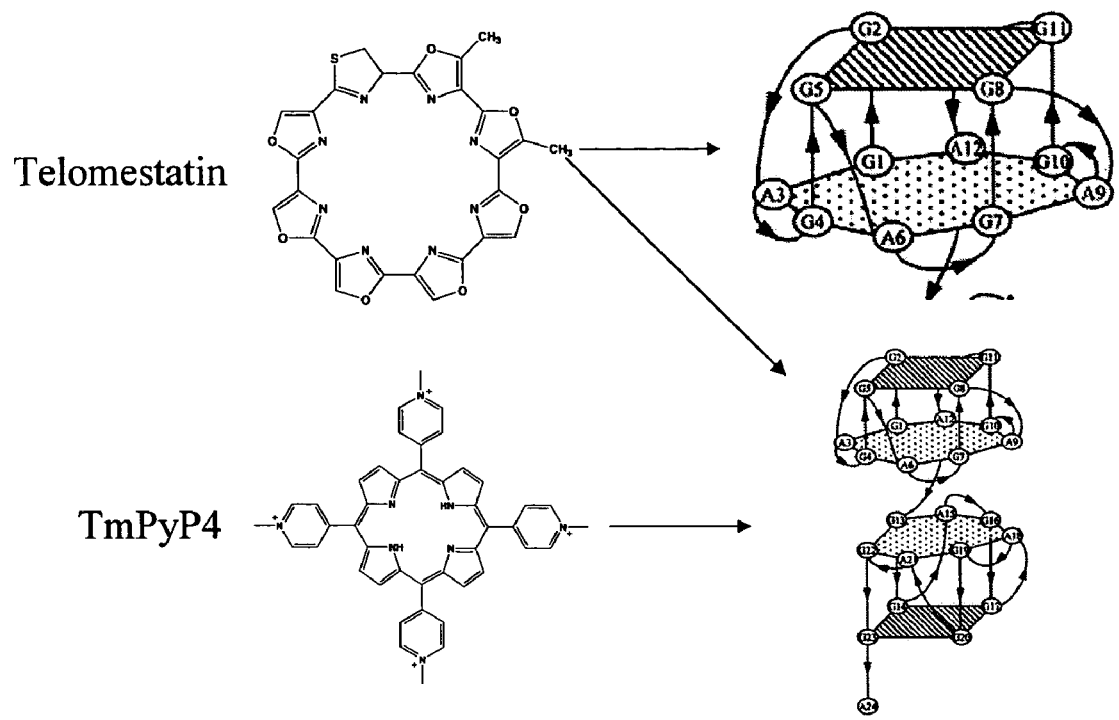
FIG. 1 depicts tetrad/heptad quadruplex conformations formed by nucleotide sequences comprising the nucleotide sequences (GGA)$_4$ (SEQ ID NO:1), (GGA)$_3$GG (SEQ ID NO:2) or (GGA)$_3$GGX$_n$(GGA)$_3$GG, where n is n is 0, 1, 2, 3, 4 or 5-10 (SEQ ID NOS:3-13). The figure also shows structures of compounds that bind to such quadruplexes.

It has been discovered that nucleic acids comprising the nucleotide sequence (GGA)$_4$ (SEQ ID NO:1) or the nucleotide sequence (GGA)$_3$GG (SEQ ID NO:2) can form biologically relevant quadruplex structures. One example of the biological relevance of such quadruplexes is the regulation of oncogene transcription. These findings lead the way to assays useful for identifying molecules that interact with such biologically relevant quadruplex structures, as well as methods for identifying and/or distinguishing related quadruplex structures formed from those sequences. These findings also are useful for methods of identifying sequences in a database that form such structures.

Nucleic Acids

Quadruplex structures can form from certain purine-rich strands in DNA. In the context of a DNA duplex, certain purine rich strands are capable of engaging in a slow equilibrium between a typical duplex helix structure and both unwound and non-B-form regions of DNA. These unwound and non-B forms can be referred to as "paranemic structures," and some forms are associated with sensitivity to S1 nuclease digestion, which can be referred to as "nuclease hypersensitivity elements" or "NHEs." A quadruplex is one type of paranemic structure and certain NHEs can adopt a quadruplex structure.

Quadruplexes can exist in different conformations, which differ in strand stoichiometry and strand orientation. FIG. 1 shows structures proposed for a guanine rich region in the c-MYC promoter region. The ability of this guanine rich DNA to adopt these structural conformations is due to the formation of guanine tetrads through Hoogsteen hydrogen bonds. Thus, one nucleic acid sequence can give rise to different quadruplex orientations, where the different conformations depend upon conditions under which they form, such as the concentration of potassium ions present in the system and the time that the quadruplex is allowed to form.

It has been discovered that nucleic acids comprising the nucleotide sequence (GGA)$_4$ (SEQ ID NO:1) or the nucleotide sequence (GGA)$_3$GG (SEQ ID NO:2) can form biologically relevant quadruplex structures. These nucleic acids adopt a quadruplex structure that differs from those reported for the c-MYC sequence, which adopts a biologically relevant chair conformation. The quadruplex structure formed by these sequences comprises a tetrad stabilized by second planar structure that is in a parallel orientation to the tetrad. The second planar structure includes five or more nucleotides in the nucleic acid and thereby forms a structure that is larger than a tetrad. For example, the second planar structure can contain five, six, seven, eight, nine, or ten nucleotides to form a pentad, hexad, heptad, octad, nonad, or dectad, respectively. Examples of heptad/tetrad quadruplex structures formed by nucleic acids having GGA repeats are shown in FIG. 1. Determining whether a nucleic acid having the nucleotide sequence (GGA)$_4$ (SEQ ID NO:1) or the nucleotide sequence (GGA)$_3$GG (SEQ ID NO:2) forms a quadruplex structure can be accomplished using methods described herein, such as by chemical footprinting methods, polymerase arrest analysis, structural spectrometric techniques and chemical binding techniques.

Different quadruplex conformations can be separately identified from one another using standard procedures known in the art, and as described herein. Also, multiple conformations can be in equilibrium with one another, and can be in equilibrium with duplex DNA if a complementary strand exists in the system. The equilibrium may be shifted to favor one conformation over another such that the favored conformation is present in a higher concentration or fraction over the other conformation or other conformations. The term "favor" as used herein refers to one conformation being at a higher concentration or fraction relative to other conformations, which is also referred to as stabilizing the particular quadruplex conformation. The term "hinder" as used herein refers to one conformation being at a lower concentration. One conformation may be favored over another conformation if it is present in the system at a fraction greater than 50%, greater than 75%, or greater than 80% or 90% with respect to another conformation (e.g., another quadruplex conformation, another paranemic conformation, or a duplex conformation). Conversely, one conformation may be hindered if it is present in the system at a fraction less than 50%, less than 25%, or less than 20% and 10%, with respect to another conformation.

Equilibrium may be shifted to favor one form over another by methods described herein. For example, certain bases in quadruplex DNA may be mutated to prevent the formation of one conformation. Typically, these mutations are located in tetrad regions of the quadruplex (regions in which four bases interact with one another in a planar orientation). In an embodiment, one or more guanine moieties in the nucleic acid are replaced with inosine moieties. Also, ion concentrations and the time with which quadruplex DNA is contacted with certain ions can favor one conformation over another. For example, potassium ions stabilize quadruplex structures, and higher concentrations of potassium ions and longer contact times of potassium ions with quadruplex DNA can favor one conformation over another. The quadruplex conformation can be favored with contact times of 5 minutes or less in solutions containing 100 mM potassium ions, and often 10 minutes or less, 20 minutes or less, 30 minutes or less, and 40 minutes or less. Potassium ion concentration and the counter anion can vary, and the skilled artisan can routinely determine which quadruplex conformation exists for a given set of conditions by utilizing the methods described herein. Furthermore, different quadruplex structures may be distinguished by probing them with molecules that favorably interact with one quadruplex form over another.

Nucleic acids often comprise or consist of DNA (e.g., genomic DNA (GDNA) or complementary DNA (cDNA)) or RNA (e.g., mRNA, tRNA, and rRNA). In embodiments where a nucleic acid is a gDNA or cDNA fragment, the fragment often is 50 or fewer, 100 or fewer, or 200 or fewer base pairs in length, and sometimes is about 300, about 400, about 500, about 600, about 700, about 800, about 900, about 1000, about 1100, about 1200, about 1300, or about 1400 base pairs in length. In an embodiment, the nucleic acid is double-stranded, and is sometimes between about 30 nucleotides to about 40 nucleotides in length. Methods for generating gDNA and cDNA fragments are known in the art (e.g., GDNA may be fragmented by shearing methods and cDNA fragment libraries are commercially available). In embodiments where the nucleic acid is a synthetically prepared fragment nucleic acid, often referred to as an "oligonucleotide," the fragment sometimes are about 30 nucleotides in length, about 40 nucleotides in length, or about 50 nucleotides in length. Synthetic oligonucleotides can be synthesized using standard methods and equipment, such as by using an ABI™3900 High Throughput DNA Synthesizer, which is available from Applied Biosystems (Foster City, CA).

Nucleic acids sometimes comprise or consist of analog or derivative nucleic acids, such as peptide nucleic acids (PNA) and others exemplified in U.S. Pat. Nos. 4,469,863; 5,536, 821; 5,541,306; 5,637,683; 5,637,684; 5,700,922; 5,717,083; 5,719,262; 5,739,308; 5,773,601; 5,886,165; 5,929,226; 5,977,296; 6,140,482; WIPO publications WO 00/56746 and WO 01/14398, and related publications. Methods for synthesizing oligonucleotides comprising such analogs or derivatives are disclosed, for example, in the patent publications cited above, in U.S. Pat. Nos. 5,614,622; 5,739,314; 5,955, 599; 5,962,674; 6,117,992; and in WO 00/75372.

In certain embodiments, nucleic acids utilized in the assays for identifying quadruplex-interacting molecules comprise or consist of a native nucleotide sequence. Native quadruplex DNA is a subsequence of cellular genomic DNA. The quadruplex DNA may be derived from genomic DNA from a cell of an organism, and often it is derived from genomic DNA of a human cell. Quadruplex DNA has been located, for example, in telomeres and in duplex DNAs that regulate gene transcription. Thus, the biological activity of quadruplexes includes regulation of gene transcription. Provided herein are quadruplex structures that are biologically relevant as they regulate gene transcription, particularly regulation of oncogenes. For example, quadruplexes are located in duplex DNA regions that regulate transcription of the genes c-MYB, HER-2/neu, EGFR, c-PIM, VAV, c-SRC and HMGA2, for example. Native quadruplex DNA may comprise or consist of the following nucleotide sequences having GGA repeats: $(GGA)_4AGA(GGA)_3GGC$ (c-MYB) (SEQ ID NO:15); $(GGA)_4$ (VAV) (SEQ ID NO:1); $AGAGAAGAGG(GGA)_5GAGG$ $AGGAGGCGC$ (HMGA2) (SEQ ID NO:16); GGAGGGGGAGGGG (human c-PIM) (SEQ ID NO:17); $AGGAGAA(GGA)_2GGT$ $(GGA)_3G_3$ (HER2/neu) (SEQ ID NO:18); $(GGA)_3AGAATGCGA(GGA)_2$ $G_3AGGAG$ (EGFR) (SEQ ID NO:19); $CCGAA(GGA)_3A(GGA)_3G_4$(c-SRC) (SEQ ID NO:20); $AGCGA(GGA)_8GAGGAA$ (SEQ ID NO:21) (osteonectin/SPARC, within −92 to −57 of the open reading frame; Oncogene 26 Jun. 2003, 22:4047-4061); $AGAAGAG(GGA)_3G$ (SEQ ID NO:22) (IL-10, within −89 to −77 of the open reading frame; J. Immunology 1 Jul. 2000, 165 :286-91); GGA A $(GGA)_3$(SEQ ID NO:23) (Decay Accelerating Factor (DAF); within −310 to −290 of the open reading frame; complementary sequence is CTCCTCCTC-CTTCCCCTCCCC (SEQ ID NO:24); Proc Natl Acad Sci 1991, 88:4675); and $(GGA)_2CCGA(GGA)_2$ (SEQ ID NO:25) (WT1; within −86 to −51 of the open reading frame; complementary sequence is $(CCT)_2GGCT(CCT)_2$ (SEQ ID NO:26); J. Biol Chem 31 Jan. 1997, 72:2901-2913). While quadruplex forming sequences typically are identified in regulatory regions upstream of a gene (e.g., a promoter or a 5' untranslated region (UTR)), quadruplex forming sequences also may be identified within a 3' UTR or within an intron or exon of a gene.

In some embodiments, test quadruplex DNA sometimes has a substantially similar nucleotide sequence to a native quadruplex DNA sequence, and often has a nucleotide sequence identical to the native quadruplex DNA sequence. A similar nucleotide sequence allows for some modifications to the native sequence so long as the test DNA is capable of adopting a quadruplex conformation, which routinely can be determined by methods described herein. Test quadruplex DNA often includes a nucleotide sequence which conforms to the motif $(GGA)_4$ (SEQ ID NO:1) or $(GGA)_3GG$ (SEQ ID NO:2) where G is guanine and A is adenine. Test quadruplex DNA may include one or more flanking nucleotides on the 5' and/or 3' end of the quadruplex which are part of the quadruplex structure or not part of the quadruplex structure. As noted above, a given nucleotide sequence can be probed as to whether it forms a quadruplex structure by carrying out chemical footprinting and polymerase arrest analyses, for example, which are discussed herein.

The term "substantially identical" refers to two or more nucleic acids sharing one or more identical nucleotide sequences. Included are nucleotide sequences that sometimes are 55%, 60%, 65%, 70%, 75%, 80%, or 85% identical to a native quadruplex-forming nucleotide sequence, and often are 90% or 95% identical to the native quadruplex-forming nucleotide sequence (each identity percentage can include a 1%, 2%, 3% or 4% variance). One test for determining whether two nucleic acids are substantially identical is to determine the percentage of identical nucleotide sequences shared between the nucleic acids.

Calculations of sequence identity can be performed as follows. Sequences are aligned for optimal comparison purposes and gaps can be introduced in one or both of a first and a second nucleic acid sequence for optimal alignment. Also, non-homologous sequences can be disregarded for comparison purposes. The length of a reference sequence aligned for comparison purposes sometimes is 30% or more, 40% or more, 50% or more, often 60% or more, and more often 70%, 80%, 90%, 100% of the length of the reference sequence. The nucleotides at corresponding nucleotide positions then are compared among the two sequences. When a position in the first sequence is occupied by the same nucleotide as the corresponding position in the second sequence, the nucleotides are deemed to be identical at that position. The percent identity between the two sequences is a function of the number of identical positions shared by the sequences, taking into account the number of gaps, and the length of each gap, introduced for optimal alignment of the two sequences.

Comparison of sequences and determination of percent identity between two sequences can be accomplished using a mathematical algorithm. Percent identity between two nucleotide sequences can be determined using the algorithm of Meyers & Miller, CABIOS 4:11-17 (1989), which has been incorporated into the ALIGN program (version 2.0), using a PAM 120 weight residue table, a gap length penalty of 12 and a gap penalty of 4. Percent identity between two nucleotide sequences can be determined using the GAP program in the GCG software package (available at http address www.gcg.com), using a NWSgapdna.CMP matrix and a gap weight of 40, 50, 60, 70, or 80 and a length weight of 1, 2, 3, 4, 5, or 6. A set of parameters often used is a Blossum 62 scoring matrix with a gap open penalty of 12, a gap extend penalty of 4, and a frameshift gap penalty of 5.

Another manner for determining if two nucleic acids are substantially identical is to assess whether a polynucleotide homologous to one nucleic acid will hybridize to the other nucleic acid under stringent conditions. As use herein, the term "stringent conditions" refers to conditions for hybridization and washing. Stringent conditions are known to those skilled in the art and can be found in *Current Protocols in Molecular Biology*, John Wiley & Sons, N.Y., 6.3.1-6.3.6 (1989). Aqueous and non-aqueous methods are described in that reference and either can be used. An example of stringent conditions is hybridization in 6×sodium chloride/sodium citrate (SSC) at about 45° C., followed by one or more washes in 0.2×SSC, 0.1% SDS at 50° C. Another example of stringent conditions are hybridization in 6×sodium chloride/sodium citrate (SSC) at about 45° C., followed by one or more washes in 0.2×SSC, 0.1% SDS at 55° C. A further example of stringent conditions is hybridization in 6×sodium chloride/sodium citrate (SSC) at about 45° C., followed by one or more washes in 0.2×SSC, 0.1% SDS at 60° C. Often, stringent conditions are hybridization in 6×sodium chloride/sodium citrate (SSC) at about 45° C., followed by one or more washes in 0.2×SSC, 0.1% SDS at 65° C. Also, stringency conditions include hybridization in 0.5M sodium phosphate, 7% SDS at 65° C., followed by one or more washes at 0.2×SSC, 1% SDS at 65° C.

Also, sequence motifs described herein may be used as "query sequences" to perform a search against public databases to identify nucleotide sequences capable of forming quadruplex structures. In certain embodiments, the query sequences are $(GGA)_4$ (SEQ ID NO:1), $(GGA)_3GG$ (SEQ ID NO:2) or $(GGA)_3GGX_n(GGA)_3GG$, where n is an integer between 1 and 3 (SEQ ID NOS:4-6), and nucleic acid comprising the nucleotide sequence is capable of forming a tetrad/heptad quadruplex structure. Such searches can be performed using the NBLAST and XBLAST programs (version 2.0) of Altschul, et al., *J. Mol. Biol.* 215:403-410 (1990). BLAST nucleotide searches can be performed with the NBLAST program, score=100, wordlength=12 to obtain nucleotide sequences homologous to nucleotide sequences from FIG. 1. To obtain gapped alignments for comparison purposes, Gapped BLAST can be utilized as described in Altschul, et al., *Nucleic Acids Res.* 25(17): 3389-3402 (1997). When utilizing BLAST and Gapped BLAST programs, default parameters of the respective programs (e.g., XBLAST and NBLAST) can be used (see, http address www.ncbi.nlm.nih.gov).

The subset of the nucleotide sequences in the database having these sequences often is subjected to a further screening process. In an embodiment, one screen is selecting sequences located adjacent to an end of an open reading frame of a gene. The subsequence is adjacent to an end of the open reading frame of the gene when an end of the subsequence is about 20, about 30, about 40, about 50, about 60, about 70, about 80, about 90, about 100, about 120, about 140, about 160, about 180, about 200, about 225, about 250, about 275, about 300, about 325, about 350, about 375, about 400, about 425, about 450, about 475, about 500, about 600, about 700, about 800, about 900, or about 1000 nucleotides from the end of the open reading frame. Another screen is selecting sequences identical to or substantially similar to known oncogene sequences. In another screening embodiment, nucleic acids comprising the identified subsequences are synthesized and are contacted with a quadruplex-interacting agent, and nucleic acids that interact with such agents are selected. In certain embodiments, the agents TMPyP4 and telomestatin are utilized, as described in the Examples section below. In this way, quadruplex-interacting agents such as telomestatin and TmPyP4 can be are utilized as "probes" of DNA secondary structure.

Another search embodiment is a gene expression profiling method using microarray analysis of global gene expression. In this embodiment, RNA from cells treated with a quadruplex-interacting agent (e.g., telomestatin or TmpyP4) is subjected to gene expression microarray analysis, and gene expression is monitored utilizing standard methods. Those genes with an altered expression of 2-fold or more in response to the agent (i.e., increased or decreased) are selected for sequence analysis. In the sequence analysis step, those nucleotide sequences having a GGA repeat in the regulatory, coding, or intronic regions of the gene are selected and subjected to further testing, such as DNA polymerase arrest analysis for interaction with the test compounds and quadruplex-interacting agents.

Candidate Molecules and Quadruplex-Interacting Molecules

Among the molecules tested in the procedures described herein, many small molecule organic compounds capable of interacting with DNA are known (see, e.g. Hurley, *Nature Rev. Cancer* 2, 188-200 (2002)), and any compounds can be selected as candidate compounds. Such compounds include small organic molecules capable of binding DNA and those that bind quadruplex DNA, such as TMPyP4, coralyne, and telomestatin (see, e.g., Shin-ya et al., *J. Am. Chem. Soc.* 123:1262 (2001); Duan et al., *Mol. Cancer Therapeutics* 1:103 (2001)). The compound may also be capable of cleaving DNA (e.g., TMPyP4). The compound also sometimes has the capability of interacting with DNA by adding a chemical moiety, such as an alkylating agent, for example. Other molecules are catalytic nucleic acids, such as ribozymes as well as an antisense nucleic acid molecules.

Candidate molecules that interact with quadruplex DNA sometimes are identified as molecules that modulate the biological activity of a native DNA, and often, such molecules stabilize the quadruplex structure. Stabilizing a quadruplex can mean that the DNA is in a quadruplex conformation with a greater frequency than it is in other paranemic conformations or duplex conformation and thereby select for the biological activity of the quadruplex structure. It is possible that certain molecules interact with more than one quadruplex conformation. A preferred class of compounds are those that interact with a quadruplex conformation.

A molecule may interact with a quadruplex DNA in a number of manners. For example, the molecule may directly bind to the quadruplex. Direct binding can be detected in various ways, including methods in which one or more labels attached to the molecule and/or quadruplex DNA, such as fluorescent, light scattering, or radioisotope labels, are detected. Binding and non-binding interactions can also be detected without labels by spectrometric methods, such as nuclear magnetic resonance, infrared, circular dichroism, and mass spectrometric methods. A molecule may bind to a quadruplex DNA by covalent or by non-covalent attractive interactions such as hydrophobic and hydrogen bond interactions.

A molecule may also interact with a quadruplex DNA by physically modifying the quadruplex and without directly binding the DNA. The quadruplex may be modified, for example, by adding a chemical moiety to the quadruplex DNA (e.g., adding one or more alkyl moieties), removing a chemical moiety from the quadruplex DNA (e.g., removing one or more bases), or cleaving the quadruplex DNA backbone. Some molecules may bind and modify the quadruplex DNA. Where a molecule modifies the quadruplex DNA, the modification may be probed to detect the interaction. For example, for a molecule that cleaves quadruplex DNA, the interaction between the molecule and the DNA can be detected by identifying cleavage products.

A candidate molecule sometimes modulates the biological activity of a quadruplex by interfering with one or more effector molecules that bring about the biological activity in conjunction with the nucleic acid capable of forming the quadruplex structure. The candidate molecule sometimes prevents binding or recognition of the effector molecule to the nucleic acid capable of forming the quadruplex structure, sometimes prevents the action of an effector molecule, and sometimes binds to an effector molecule, the nucleic acid having the quadruplex formed or not formed, or a combination of the foregoing.

Candidate molecules often are organic or inorganic compounds having a molecular weight of 10,000 grams per mole or less, and sometimes having a molecular weight of 5,000 grams per mole or less, 1,000 grams per mole or less, or 500 grams per mole or less. Also included are salts, esters, and other pharmaceutically acceptable forms of the compounds. Compounds that interact with nucleic acids are known in the art (see, e.g., Hurley, *Nature Rev. Cancer* 2:188-200 (2002); Anantha, et al., *Biochemistry* Vol. 37, No. 9:2709-2714 (1998); and Ren, et al., *Biochemistry* 38:16067-16075 (1999)).

Compounds can be obtained using known combinatorial library methods, including spatially addressable parallel solid phase or solution phase libraries; synthetic library methods requiring deconvolution; "one-bead one-compound" library methods; and synthetic library methods using affinity chromatography selection. Examples of methods for synthesizing molecular libraries are described, for example, in DeWitt, et al., *Proc. Natl. Acad. Sci. U.S.A.* 90:6909 (1993); Erb, et al., *Proc. Natl. Acad. Sci. USA* 91:11422 (1994); Zuckermann, et al., *J. Med. Chem.*37:2678 (1994); Cho, et al., *Science* 261: 1303 (1993); Carrell, et al., *Angew. Chem. Int. Ed. Engl.* 33:2059 (1994); Carell, et al., *Angew. Chem. Int. Ed. Engl.* 33:2061 (1994); and Gallop, et al., *J. Med. Chem.* 37:1233 (1994).

In addition to an organic and inorganic compound, a candidate molecule sometimes is a nucleic acid, a catalytic nucleic acid (e.g., a ribozyme), a small interfering RNA (siR-NAs), a nucleotide, a nucleotide analog, a polypeptide, an antibody, or a peptide mimetic. Methods for making and using these molecules are known in the art. For example, methods for making ribozymes and assessing ribozyme activity are described (see e.g., U.S. Pat. Nos. 5,093,246; 4,987, 071; and 5,116,742; Haselhoff & Gerlach, *Nature* 334:585-591 (1988) and Bartel & Szostak, *Science* 261:1411-1418 (1993)). Also, methods for generating siRNA are known (see e.g., Elbashir, et al., *Methods* 26:199-213 (2002) and http address www.dharmacon.com) and peptide mimetic libraries are described (see, e.g., Zuckermann, et al., *J. Med. Chem.* 37:2678-2685 (1994)).

Biological Activity of Nucleic Acids

Determining whether the biological activity of a native quadruplex DNA is modulated in a cell, tissue, or organism can be accomplished by monitoring modulation of a signal in an in vitro or in vivo assay. The signal in the assay sometimes is generated or modulated by transcription of the nucleic acid, binding of a protein to the nucleic acid, a fluorophore incorporated in the nucleic acid, or cell proliferation, for example. Transcription can be detected, for example, by directly detecting RNA transcripts or detecting polypeptides translated by transcripts, which are methods known in the art.

Candidate molecules, some identified by the procedures described above, sometimes are screened in in vitro or in vivo assays to determine whether they modulate the biological activity of the nucleic acid. Candidate molecules and nucleic acids can be added to an assay system in any order to determine whether the candidate molecule modulates the biological activity of the nucleic acid. For example, a candidate molecule sometimes is added to an assay system before, simultaneously, or after a nucleic acid is added.

In these assays, candidate molecules are contacted with the nucleic acid in the assay system, where the term "contacting" refers to placing a candidate molecule in close proximity to a nucleic acid and allowing the assay components to collide with one another, often by diffusion. Contacting these assay components with one another can be accomplished by adding them to a body of fluid or in a reaction vessel, for example. The components in the system may be mixed in variety of manners, such as by oscillating a vessel, subjecting a vessel to a vortex generating apparatus, repeated mixing with a pipette or pipettes, or by passing fluid containing one assay component over a surface having another assay component immobilized thereon, for example.

As used herein, the term "system" refers to an environment that receives the assay components, which includes, for example, microtitre plates (e.g., 96-well or 384-well plates), silicon chips having molecules immobilized thereon and optionally oriented in an array (see, e.g., U.S. Pat. No. 6,261, 776 and Fodor, *Nature* 364:555-556 (1993)), and microfluidic devices (see, e.g., U.S. Pat. Nos. 6,440,722; 6,429,025; 6,379,974; and 6,316,781). The system can include attendant equipment for carrying out the assays, such as signal detectors, robotic platforms, and pipette dispensers.

One or more assay components (e.g., the nucleic acid, candidate molecule or nucleic acid binding protein) sometimes are immobilized to a solid support. The attachment between an assay component and the solid support often is covalent and sometimes is non-covalent (see, e.g., U.S. Pat. No. 6,022,688 for non-covalent attachments). The solid support often is one or more surfaces of the system, such as one or more surfaces in each well of a microtiter plate, a surface of a silicon wafer, a surface of a bead (see, e.g., Lam, *Nature* 354: 82-84 (1991)) optionally linked to another solid support, or a channel in a microfluidic device, for example. Types of solid supports, linker molecules for covalent and non-covalent attachments to solid supports, and methods for immobilizing nucleic acids and other molecules to solid supports are known (see, e.g., U.S. Pat. Nos. 6,261,776; 5,900,481; 6,133, 436; and 6,022,688; and WIPO publication WO 01/18234).

Protein molecules sometime are contacted with the nucleic acid. Polypeptide molecules sometimes are added to the system in free form, and sometimes are linked to a solid support or another molecule. For example, polypeptide test molecules sometimes are linked to a phage via a phage coat protein. The latter embodiment often is accomplished by using a phage display system, where nucleic acids linked to a solid support are contacted with phages that display different polypeptide candidate molecules. Phages displaying polypeptide candidate molecules that interact with the immobilized nucleic acids adhere to the solid support, and phage nucleic acids corresponding to the adhered phages then are isolated and sequenced to determine the sequence of the polypeptide test molecules that interacted with the immobilized nucleic acids. Methods for displaying a wide variety of peptides or proteins as fusions with bacteriophage coat proteins are known (Scott and Smith, *Science* 249:386-390 (1990); Devlin, Science 249:404-406 (1990); Cwirla, et al., *Proc. NatL. Acad. Sci.* 87:6378-6382 (1990); Felici, *J. Mol. Biol.* 222:301-310 (1991); U.S. Patent Nos. 5,096,815 and 5,198,346; U.S. Pat. Nos. 5,223,409; 5,403,484; 5,571,698; and 5,766,905). Methods also are available for linking the test polypeptide to the N-terminus or the C-terminus of the phage coat protein.

A signal generated by the system when a candidate molecule binds to a nucleic acid and/or a nucleic acid binding protein often scales directly with a range of increasing nucleic acid, nucleic acid binding protein, or candidate molecule concentrations. Signal intensity often exhibits a hyperbolic relationship when plotted as a function of nucleic acid, candidate molecule, or nucleic acid binding protein concentrations. The signal sometimes is increased relative to background signal levels when a candidate molecule binds to a nucleic acid and/or a nucleic acid binding protein, and sometimes the signal decreases relative to background signal levels under such circumstances. The candidate molecules often interact with the nucleic acid and/or nucleic acid binding protein by reversible binding, and sometimes interact with irreversible binding. For example, the candidate molecule may reversibly form a covalent bond between a portion of the candidate molecule and an amino acid side chain in the protein (e.g., a lysine), depending on the chemical structure of the candidate molecule.

Candidate molecules often are identified as interacting with the nucleic acid and/or a nucleic acid binding protein when the signal produced in a system containing the candidate molecule is different than the signal produced in a system not containing the candidate molecule. While background signals may be assessed each time a new candidate molecule, nucleic acid, or nucleic acid binding protein is probed by the assay, detecting the background signal is not required each time a new test molecule or test nucleic acid is assayed. Control assays also can be performed to determine background signals and to rule out false positive results and false negative results. Such control assays often do not include one or more assay components included in other assays (e.g., a control assay sample sometimes does not include a candidate molecule, a nucleic acid, or a protein that interacts with the nucleic acid).

In addition to determining whether a candidate molecule gives rise to a different signal, the affinity of the interaction between the candidate molecule with the nucleic acid and/or nucleic acid binding protein sometimes is quantified. $IC_{50}$, $K_d$, or $K_i$ threshold values sometimes are compared to the measured $IC_{50}$ or $K_d$ values for each interaction, and thereby are used to identify a candidate molecule that interacts with the nucleic acid or nucleic acid binding protein and modulates the biological activity. For example, $IC_{50}$ or $K_d$ threshold values of 10 μM or less, 1 μM or less, and 100 nM or less often are utilized, and sometimes threshold values of 10 nM or less, 1 nM or less, 100 pM or less, and 10 pM or less are utilized to identify candidate molecules that interact with nucleic acids and/or binding proteins and modulate the biological activity.

Specific assays sometimes are utilized to identify candidate molecules that modulate the biological activity of a nucleic acid capable of forming a quadruplex. For example, fluorescence assays, gel mobility shift assays (see, e.g., Jin & Pike, *Mol. Endocrinol.* 10:196-205 (1996) and Postel, *J. Biol. Chem.* 274:22821-22829 (1999)), polymerase arrest assays, transcription reporter assays, DNA cleavage assays, protein binding and apoptosis assays (see, e.g., Amersham Biosciences (Piscataway, N. J.)) sometimes are utilized. Also, topoisomerase assays sometimes are utilized subsequently to determine whether the quadruplex interacting molecules have a topoisomerase pathway activity (see, e.g., TopoGEN, Inc. (Columbus, Ohio)).

A gel electrophoretic mobility shift assay (EMSA) is useful for determining whether a nucleic acid forms a quadruplex and whether a nucleotide sequence is quadruplex-destabilizing. EMSA is conducted as described previously (Jin & Pike, *Mol. Endocrinol.* 10:196-205 (1996)) with minor modifications. Synthetic single-stranded oligonucleotides are labeled in the 5' terminus with T4-kinase in the presence of [γ-$^{32}$P] ATP (1,000 mCi/mmol, Amersham Life Science) and purified through a sephadex column. $^{32}$P-labeled oligonucleotides (~30,000 cpm) then are incubated with or without various concentrations of a testing compound in 20 μl of a buffer containing 10 mM Tris pH 7.5, 100 mM KCl, 5 mM dithiothreitol, 0.1 mM EDTA, 5 mM MgCl$_2$, 10% glycerol, 0.05% Nonedit P-40, and 0.1 mg/ml of poly(dI-dC) (Pharmacia). After incubation for 20 minutes at room temperature, binding reactions are loaded on a 5% polyacrylamide gel in 0.25 ×Tris borate-EDTA buffer (0.25 ×TBE, 1 ×TBE is 89 mM Trisborate, pH 8.0 mM EDTA). The gel is dried and each band is quantified using a phosphorimager.

Another example of an EMSA assay is performed as follows. Ten microliter reactions are assembled in Reaction Buffer (50 mM Tris-HCl, pH 7.9, 0.5 mM dithiothreitol, and 50 mg/ml bovine serum albumin). MgCl$_2$, KCl, EDTA, protease K, and ATP are added. Radiolabeled DNA or fluorescently labeled DNA (described above) and NM23-H2 in storage buffer (20 mM Hepes, pH 7.9, 5 mM MgCl$_2$, 0.1 mM EDTA, 0.1 M KCl, 1 mM dithiothreitol, 20% glycerol, and protease inhibitors (Postel, et al., *Mol. Cell. Biol.* 9:5123-5133 (1989)) are added last, and the reactions are incubated for 15 minutes at room temperature. To separate the protein-DNA complexes, the reactions are loaded onto 5% native polyacrylamide gels and electrophoresed in 0.53 TBE buffer (45 mM Tris borate, pH 8.3, 1.25 mM EDTA) at room temperature for 30 minutes at 100 V. Gels are vacuum-dried and exposed onto XAR (Eastman Kodak Co.) film.

Chemical footprinting assays are useful for assessing quadruplex structure. Quadruplex structure is assessed by determining which nucleotides in a nucleic acid is protected or unprotected from chemical modification as a result of being inaccessible or accessible, respectively, to the modifying reagent. A DMS methylation assay is an example of a chemical footprinting assay. In such an assay, bands from EMSA are isolated and subjected to DMS-induced strand cleavage. Each band of interest is excised from an electrophoretic mobility shift gel and soaked in 100 mM KCl solution (300 μl) for 6 hours at 4° C. The solutions are filtered (microcentrifuge) and 30,000 cpm (per reaction) of DNA solution is diluted further with 100 mM KCl in 0.1×TE to a total volume of 70 μl (per reaction). Following the addition of 1 μl salmon sperm DNA (0.1 μg/μl), the reaction mixture is incubated with 1 μl DMS solution (DMS:ethanol; 4:1; v:v) for a period of time. Each reaction is quenched with 18 μl of stop buffer (β-mercaptoathanol:water:NaOAc (3 M); 1:6:7; v:v:v). Following ethanol precipitation (twice) and piperidine cleavage, the reactions are separated on a preparative gel (16%) and visualized on a phosphorimager.

A polymerase arrest assay is useful for determining whether transcription is modulated by a candidate molecule and/or a nucleic acid binding protein. Such an assay includes a template nucleic acid, which often comprises a quadruplex forming sequence, and a primer nucleic acid which hybridizes to the template nucleic acid 5' of the quadruplex-forming sequence. The primer is extended by a polymerase (e.g., Taq polymerase), which advances from the primer along the template nucleic acid. In this assay, a quadruplex structure can block or arrest the advance of the enzyme, leading to shorter transcription fragments. Also, the arrest assay may be conducted at a variety of temperatures, including 45° C. and 60° C., and at a variety of ion concentrations. An example of the Taq polymerase stop assay is described in Han, et al., *Nucl. Acids Res.* 27:537-542 (1999), which is a modification of that used by Weitzmann, et al., *J. Biol. Chem.* 271, 20958-20964 (1996). Briefly, a reaction mixture of template DNA (50 nM), Tris○HCl (50 mM), MgCl$_2$ (10 mM), DTT (0.5 mM), EDTA (0.1 mM), BSA (60 ng), and 5'-end-labeled quadruplex nucleic acid (~18 nM) is heated to 90° C. for 5 minutes and allowed to cool to ambient temperature over 30 minutes. Taq Polymerase (1 μl) is added to the reaction mixture, and the reaction is maintained at a constant temperature for 30 minutes. Following the addition of 10 μl stop buffer (formamide (20 ml), 1 M NaOH (200 μl), 0.5 M EDTA (400 μl), and 10 mg bromophenol blue), the reactions are separated on a preparative gel (12%) and visualized on a phosphorimager. Adenine sequencing (indicated by "A" at the top of the gel) is performed using double-stranded DNA Cycle Sequencing System from Life Technologies. The general sequence for the template strands is TCCAACTATGTATAC-INSERT-TTAGCGACACGCAATTGCTATAGTGAGTCGTATTA (SEQ ID NOS:27-28). Bands on the gel that exhibit slower mobility are indicative of quadruplex formation. Bands on the gel that exhibit slower mobility are indicative of quadruplex formation.

Certain arrest assays are performed in cells. In a transcription reporter assay, test quadruplex DNA is coupled to a reporter system, such that a formation or stabilization of a quadruplex structure can modulate a reporter signal. An example of such a system is a reporter expression system in which a polypeptide, such as luciferase or green fluorescent protein (GFP), is expressed by a gene operably linked to the potential quadruplex forming nucleic acid and expression of the polypeptide can be detected. As used herein, the term "operably linked" refers to a nucleotide sequence which is regulated by a sequence comprising the potential quadruplex forming nucleic acid. A sequence may be operably linked when it is on the same nucleic acid as the quadruplex DNA, or on a different nucleic acid. An exemplary luciferase reporter system is described herein. A luciferase promoter assay described in He, et al., *Science* 281:1509-1512 (1998) often is utilized for the study of quadruplex formation. Specifically, a vector utilized for the assay is set forth in reference 11 of the He, et al., document. In this assay, HeLa cells are transfected using the lipofectamin 2000-based system (Invitrogen) according to the manufacturer's protocol, using 0.1 µg of pRL-TK (Renilla luciferase reporter plasmid) and 0.9 µg of the quadruplex-forming plasmid. Firefly and Renilla luciferase activities are assayed using the Dual Luciferase Reporter Assay System (Promega) in a 96-well plate format according to the manufacturer's protocol.

Circular dichroism (CD) sometimes is utilized to determine whether another molecule interacts with a quadruplex nucleic acid. CD is particularly useful for determining whether a candidate molecule interacts with a nucleic acid in vitro. In certain embodiments, a candidate molecule is added to a DNA sample (5 µM each) in a buffer containing 10 mM potassium phosphate (pH 7.2) and 10 or 250 mM KCl at 37° C. and then allowed to stand for 5 min at the same temperature before recording spectra. CD spectra are recorded on a Jasco J-715 spectropolarimeter equipped with a thermoelectrically controlled single cell holder. CD intensity normally is detected between 220 nm and 320 nm and comparative spectra for DNA alone, candidate molecule alone, and the DNA with the candidate molecule are generated to determine the presence or absence of an interaction (see, e.g., Datta, et al., *JACS*123:9612-9619 (2001)). Spectra are arranged to represent the average of eight scans recorded at 100 nm/min.

An example of a fluorescence binding assay is a system that includes a nucleic acid, a signal molecule, and a candidate molecule. The signal molecule generates a fluorescent signal when bound to the nucleic acid (e.g., N-methylmesoporphyrin IX (NMM)), and the signal is altered when a candidate compound competes with the signal molecule for binding to the nucleic acid. An alteration in the signal when a candidate molecule is present as compared to when the candidate molecule is not present identifies the candidate molecule as a nucleic acid-interacting molecule. 50 µl of nucleic acid is added in 96-well plate. A candidate molecule also is added in varying concentrations. A typical assay is carried out in 100 l of 20 mM HEPES buffer, pH 7.0, 140 mM NaCl, and 100 mM KCl. 50 µl of the signal molecule NMM then is added for a final concentration of 3 µM. NMM is obtained from Frontier Scientific Inc, Logan, Utah. Fluorescence is measured at an excitation wavelength of 420 nm and an emission wavelength of 660 nm using a FluroStar 2000 fluorometer (BMG Labtechnologies, Durham, NC). Fluorescence often is plotted as a function of concentration of the candidate molecule or nucleic acid and maximum fluorescent signals for NMM are assessed in the absence of these molecules.

A cell proliferation assay is useful for assessing the utility of a candidate molecule for treating a cell proliferative disorder in a subject. In a cancer cell proliferation assay, cell proliferation rates are assessed as a function of different concentrations of test compounds added to the cell culture medium. Any cancer cell type can be utilized in the assay. In one embodiment, colon cancer cells are cultured in vitro and test compounds are added to the culture medium at varying concentrations. A useful colon cancer cell line is colo320, which is a colon adenocarcinoma cell line deposited with the National Institutes of Health as accession number JCRB0225. Parameters for using such cells are available at the http address cellbank.nihs.go.jp/cell/data/jcrbO225. htm. Another useful cell line is colo 205 described hereafter.

Utilization of Candidate Molecules

Because quadruplexes are regulators of biological processes such as oncogene transcription, modulators of quadruplex biological activity can be utilized as cancer therapeutics. For example, molecules that stabilize quadruplex structures can exert a therapeutic effect for certain cell proliferative disorders and related conditions because quadruplex structures typically down-regulate the oncogene expression which can cause cell proliferative disorders. Quadruplex-interacting candidate molecules can exert a biological effect according to different mechanisms, which include, for example, stabilizing a native quadruplex structure, inhibiting conversion of a native quadruplex to duplex DNA, and stabilizing a native quadruplex structure having a quadruplex-destabilizing nucleotide substitution. Thus, quadruplex interacting candidate molecules described herein may be administered to cells, tissues, or organisms, thereby down-regulating oncogene transcription and treating cell proliferative disorders. The terms "treating," "treatment" and "therapeutic effect" as used herein refer to reducing or stopping a cell proliferation rate (e.g., slowing or halting tumor growth) or reducing the number of proliferating cancer cells (e.g., removing part or all of a tumor) and refers to alleviating, completely or in part, a cell proliferation condition.

Quadruplex interacting molecules and quadruplex forming nucleic acids can be utilized to target a cell proliferative disorder. Cell proliferative disorders include, for example, colorectal cancers. Other examples of cancers include hematopoietic neoplastic disorders, which are diseases involving hyperplastic/neoplastic cells of hematopoietic origin (e.g., arising from myeloid, lymphoid or erythroid lineages, or precursor cells thereof). The diseases can arise from poorly differentiated acute leukemias, e.g., erythroblastic leukemia and acute megakaryoblastic leukemia. Additional myeloid disorders include, but are not limited to, acute promyeloid leukemia (APML), acute myelogenous leukemia (AML) and chronic myelogenous leukemia (CML) (reviewed in Vaickus, Crit. Rev. in *Oncol./Hemotol.* 11:267-297 (1991)); lymphoid malignancies include, but are not limited to acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease. Cell proliferative disorders also include cancers of the colorectum, breast, lung, liver, pancreas, lymph node, colon, prostate, brain, head and neck, skin, liver, kidney, and heart. Candidate molecules also can be utilized to target cancer related processes and conditions, such as increased angiogenesis, by inhibiting angiogenesis in a subject.

Thus, provided herein are methods for reducing cell proliferation or for treating or alleviating cell proliferative disorders, which comprise contacting a system having a nucleic acid comprising a native quadruplex with a candidate molecule identified herein. The system sometimes is a group of cells or one or more tissues, and often is a subject in need of a treatment of a cell proliferative disorder. A subject often is a mammal such as a mouse, rat, monkey, or human. One embodiment is a method for treating a cell proliferative disorder associated with disregulation of a gene having a $(GGA)_4$ (SEQ ID NO:1) or $(GGA)_3GG$ (SEQ ID NO:2) sequence or in proximity to a $(GGA)_4$ (SEQ ID NO:1) or $(GGA)_3GG$ (SEQ ID NO:2) sequence, such as c-MYB, HER-2/neu, EGFR, c-PIM, VAV c-SRC, HMGA2, osteonectin/SPARC, IL-10, DAF and/or WT1.

Any suitable formulation of the candidate molecules described herein can be prepared for administration. Any suitable route of administration may be used, including but not limited to oral, parenteral, intravenous, intramuscular, topical and subcutaneous routes.

In cases where candidate molecules are sufficiently basic or acidic to form stable nontoxic acid or base salts, administration of the candidate molecules as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts. Pharmaceutically acceptable salts are obtained using standard procedures well known in the art, for example by reacting a sufficiently basic candidate molecule such as an amine with a suitable acid affording a physiologically acceptable anion. Alkali metal (e.g., sodium, potassium or lithium) or alkaline earth metal (e.g., calcium) salts of carboxylic acids also are made.

In one embodiment, a candidate molecule is administered systemically (e.g., orally) in combination with a pharmaceutically acceptable vehicle such as an inert diluent or an assimilable edible carrier. They may be enclosed in hard or soft shell gelatin capsules, compressed into tablets, or incorporated directly with the food of the patient's diet. For oral therapeutic administration, the active candidate molecule may be combined with one or more excipients and used in the form of ingestible tablets, buccal tablets, troches, capsules, elixirs, suspensions, syrups, wafers, and the like. Such compositions and preparations should contain at least 0.1% of active candidate molecule. The percentage of the compositions and preparations may be varied and may conveniently be between about 2 to about 60% of the weight of a given unit dosage form. The amount of active candidate molecule in such therapeutically useful compositions is such that an effective dosage level will be obtained.

Tablets, troches, pills, capsules, and the like also may contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active candidate molecule, sucrose or fructose as a sweetening agent, methyl and propylparabens as preservatives, a dye and flavoring such as cherry or orange flavor. Any material used in preparing any unit dosage form is pharmaceutically acceptable and substantially non-toxic in the amounts employed. In addition, the active candidate molecule may be incorporated into sustained-release preparations and devices.

The active candidate molecule also may be administered intravenously or intraperitoneally by infusion or injection. Solutions of the active candidate molecule or its salts may be prepared in a buffered solution, often phosphate buffered saline, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms. The candidate molecule is sometimes prepared as a polymatrix-containing formulation for such administration (e.g., a liposome or microsome). Liposomes are described for example in U.S. Pat. No. 5,703,055 (Felgner, et al.) and Gregoriadis, Liposome Technology vols. I to III (2nd ed. 1993).

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active candidate molecule in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present candidate molecules may be applied in liquid form. Candidate molecules often are administered as compositions or formulations, in combination with a dermatologically acceptable carrier, which may be a solid or a liquid. Examples of useful dermatological compositions used to deliver candidate molecules to the skin are known (see, e.g., Jacquet, et al. (U.S. Pat. No. 4,608,392), Geria (U.S. Pat. No. 4,992,478), Smith, et al. (U.S. Pat. No. 4,559,157) and Wortzman (U.S. Pat. No. 4,820,508).

Candidate molecules may be formulated with a solid carrier, which include finely divided solids such as talc, clay, microcrystalline cellulose, silica, alumina and the like. Useful liquid carriers include water, alcohols or glycols or water-alcohol/glycol blends, in which the present candidate molecules can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Generally, the concentration of the candidate molecule in a liquid composition often is from about 0.1 wt % to about 25 wt %, sometimes from about 0.5 wt % to about 10 wt %. The concentration in a semi-solid or solid composition such as a gel or a powder often is about 0.1 wt % to about 5 wt %, sometimes about 0.5 wt % to about 2.5 wt %. A candidate molecule composition may be prepared as a unit dosage form, which is prepared according to conventional techniques known in the pharmaceutical industry. In general terms, such techniques include bringing a candidate molecule into association with pharmaceutical carrier(s) and/or excipient(s) in liquid form or finely divided solid form, or both, and then shaping the product if required. The candidate molecule composition may be formulated into any dosage form, such as tablets, capsules, gel capsules, liquid syrups, soft gels, suppositories, and enemas. The compositions also may be formulated as suspensions in aqueous, non-aqueous, or mixed media. Aqueous suspensions may further contain substances which increase viscosity, including for example, sodium carboxymethylcellulose, sorbitol, and/or dextran. The suspension may also contain one or more stabilizers.

The amount of the candidate molecule, or an active salt or derivative thereof, required for use in treatment will vary not only with the particular salt selected but also with the route of administration, the nature of the condition being treated and the age and condition of the patient and will be ultimately at the discretion of the attendant physician or clinician.

A useful candidate molecule dosage often is determined by assessing its in vitro activity in a cell or tissue system and/or in vivo activity in an animal system. For example, methods for extrapolating an effective dosage in mice and other animals to humans are known to the art (see, e.g., U.S. Pat. No. 4,938,949). Such systems can be used for determining the $LD_{50}$ (the dose lethal to 50% of the population) and the $ED_{50}$ (the dose therapeutically effective in 50% of the population) of a candidate molecule. The dose ratio between a toxic and therapeutic effect is the therapeutic index and it can be expressed as the ratio $ED_{50}/LD_{50}$. The candidate molecule dosage often lies within a range of circulating concentrations for which the $ED_{50}$ is associated with little or no toxicity. The dosage may vary within this range depending upon the dosage form employed and the route of administration utilized. For any candidate molecules used in the methods described herein, the therapeutically effective dose can be estimated initially from cell culture assays. A dose sometimes is formulated to achieve a circulating plasma concentration range covering the $IC_{50}$ (i.e., the concentration of the test candidate molecule which achieves a half-maximal inhibition of symptoms) as determined in in vitro assays, as such information often is used to more accurately determine useful doses in humans. Levels in plasma may be measured, for example, by high performance liquid chromatography.

Another example of effective dose determination for a subject is the ability to directly assay levels of "free" and "bound" candidate molecule in the serum of the test subject. Such assays may utilize antibody mimics and/or "biosensors" generated by molecular imprinting techniques. The candidate molecule is used as a template, or "imprinting molecule", to spatially organize polymerizable monomers prior to their polymerization with catalytic reagents. Subsequent removal of the imprinted molecule leaves a polymer matrix which contains a repeated "negative image" of the candidate molecule and is able to selectively rebind the molecule under biological assay conditions (see, e.g., Ansell, et al., *Current Opinion in Biotechnology* 7: 89-94 (1996) and in Shea, *Trends in Polymer Science* 2: 166-173 (1994)). Such "imprinted" affinity matrixes are amenable to ligand-binding assays, whereby the immobilized monoclonal antibody component is replaced by an appropriately imprinted matrix (see, e.g., Vlatakis, et al., *Nature* 361: 645-647 (1993)). Through the use of isotope-labeling, "free" concentration of candidate molecule can be readily monitored and used in calculations of $IC_{50}$. Such "imprinted" affinity matrixes can also be designed to include fluorescent groups whose photon-emitting properties measurably change upon local and selective binding of candidate molecule. These changes can be readily assayed in real time using appropriate fiber optic devices, in turn allowing the dose in a test subject to be quickly optimized based on its individual $IC_{50}$. An example of such a "biosensor" is discussed in Kriz, et al., *Analytical Chemistry* 67:2142-2144 (1995).

Exemplary doses include milligram or microgram amounts of the candidate molecule per kilogram of subject or sample weight, for example, about 1 microgram per kilogram to about 500 milligrams per kilogram, about 100 micrograms per kilogram to about 5 milligrams per kilogram, or about 1 microgram per kilogram to about 50 micrograms per kilogram. It is understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid described herein, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific candidate molecule employed, the age, body weight, general health, gender, and diet of the subject, the time of administration, the route of administration, the rate of excretion, any drug combination, and the degree of expression or activity to be modulated.

The invention is further illustrated by the following examples which should not be construed as limiting. The contents of the documents cited in this document are incorporated herein by reference.

EXAMPLES

The following examples were performed in part using single stranded DNA templates representing promoter regions of the HER-2/neu and c-MYB oncogenes. The HER-2/neu oncogene promoter contains a 28 base pair homopurine/homopyrimidine tract characterized by multiple GGA trinucleotide repeats. Similarly, the c-MYB oncogene promoter contains a 54 base pair homopurine/homopyrimidine tract also characterized by multiple GGA trinucleotide repeats. The sequence of purine rich oligonucleotides representing the purine rich strands of the HER-2/neu and c-MYB promoters are illustrated in this figure. The quadruplex forming regions described herein are highlighted and share an 11 nucleotide sequence motif: GGAGGAGGAGG (SEQ ID NO:2). The HER-2/neu promoter contains one of these motifs, and the c-MYB promoter contains three of these motifs.

The purine rich tract containing the GGA repeats is located between the TATA and CCAT boxes. The beginning of this purine rich tract can serve as an alternate transcription initiator and the entire polypurine:polypyrimidine tract has been described as a docking site for nuclear matrix attachment that can recruit the transcription factor NFkB to regulate HER-2/neu expression. The c-MYB promoter is a "TATA-less" promoter that initiates transcription upstream of the GGA repeat elements. The relationship between the most upstream putative quadruplex forming region of the c-MYB promoter and the transcription start site is approximately 15 nucleotides, almost identical to the distance between the putative quadruplex forming region of the HER-2/neu promoter and the alternate transcription start site. These GGA repeats represent novel initiator elements.

Several nucleic acids are utilized in the examples below. One nucleic acid is HNP36 (named for HER-2/neu promoter, 36-mer), which contains a polypurine tract from a region located at positions −218 to −245 relative to the translation start site of HER-2/neu and the 4 flanking bases on either side of the tract. The HNP36 nucleic acid consists of the sequence 5'-TCACAGGAGAAGGAGGAGGT GGAGGAGGCTCG 3' (SEQ ID NO:29). Another HER-2/neu nucleic acid utilized for polymerase arrest assays is designated HNP86 (HER-2/neu promoter, 86-mer), which contains the polypurine tract of HER-2/neu inserted into a common sequence used for such assays, and consists of the sequence 5'-TCCAACTATG-TATACTCACAGGAGAA GGAGGAGGTGGAGGAG-GAGGGCTGCTTAGCGGCACGCAATTGC-TATAGTGAGTCGTATTA-3'(SEQ ID NO:30). Another nucleic acid is designated c-MYB 66, a 66-mer representing the polypurine tract of the c-MYB promoter: 5'-TTTCTCAG-GAGAAAGAGGAGGAGGAGGA GGTCACGGAGGAG-GAGGAGGAGAAGGAGGAGGAGGAGGAAA-CAGGTT-3' (SEQ ID NO:31). A c-MYB sequence utilized for polymerase arrest assays is a 100-mer that includes a cassette commonly utilized for such assays and has the sequence: 5'-TCCAACTATGTATACTTTCTCAGGA GAAAGAGGAGGAGGAGGAGGTCACGGAG-GAGGAGGAGGAGAAGGAGGAGGA GGAGGAAA-CAGGTTTTAGCGACATTGCTATAGTGAGTCGTATTA-3' (SEQ ID NO:32).

Example 1

Structural Determination of Quadruplex DNA

Electrophoretic mobility shift assays (EMSAs) were performed on single stranded DNA oligonucleotides representing purine rich tracts containing the GGA repeat regions of the HER-2/neu promoter and the c-MYB promoter. These studies demonstrated the presence of a potassium dependent DNA structure of lower electrophoretic mobility in both the HER-2/neu and c-MYB sequences.

Electrophoresis mobility shift analysis (EMSA) and DMS footprint analysis indicating potassium dependent quadruplex formation in the HER-2/neu promoter were performed. In the EMSA the presence of a high molecular weight species becomes prominent only in the presence of potassium. EMSA was carried-out by gel electrophoresis (16%, 12.5 mM KCl/NaCl, 16 h, 4° C.) of 3'-end-labeled nucleic acids incubated in the presence of 100 mM KCl. The DMS footprint data and the EMSA data show that an intramolecular quadruplex formed. Usually, intramolecular quadruplex are compact structure that migrate more rapidly than single stranded DNA on EMSAs. A slower migrating species identified in the analysis is a multimer of the intramolecular quadruplex, most likely a stacked dimer of the heptad:tetrad.

For DMS footprinting analyses, bands from EMSA were isolated and subjected to DMS-induced strand cleavage. Each band of interest was excised and soaked in 100 mM KCl solution (300 µl) for 6 hr at 4° C. The solutions were filtered (microcentrifuge) and 30,000 cpm (per reaction) of DNA solution was diluted further with 100 mM KCl in 0.1 ×TE to a total volume of 70 µl (per reaction). Following the addition of 1 µl salmon sperm DNA (0.1 µg/µl), the reaction mixture was subjected to 1 µl DMS solution (DMS:ethanol; 4:1; v:v). Each reaction was quenched with 18 µl of stop buffer (β-mercaptoethanol:water:NaOAc (3 M); 1:6:7 v:v:v). Following ethanol precipitation (twice) and piperidine cleavage, the reactions were separated on a preparative gel (16%) and visualized on a phosphorimager.

EMSA also demonstrated that treatment of the oligonucleotides with dimethyl sulfate (DMS), which methylated the N7 position of guanines, prevented the altered mobility. Quadruplex formation depends on the formation of Hoogsteen hydrogen bonds by the N7 position of each guanine in the tetrad (or heptad). Methylation of the guanines prior to incubation with potassium prevented the formation of the DNA secondary structure, suggesting a multimer of an intramolecular quadruplex.

To further identify the DNA secondary structures formed in the EMSA analysis, the individual bands from the EMSA were excised and probed with DMS. In the presence of potassium, the HER-2/neu promoter gave rise to a single footprint at the $(GGA)_3GG$ (SEQ ID NO:2) sequence. The HER-2/neu footprint also contained three hypersensitive adenines corresponding exactly to the adenine bases postulated to be involved in the G:A:G:A:G:A:G heptad of the heptad:tetrad structure. The c-MYB promoter produced two potassium dependent footprints corresponding to two sets of $(GGA)_3GG$ (SEQ ID NO:2) sequences in the c-MYB promoter sequence. Two of three identical regions having these GGA triplet repeats produced a footprint. The EMSA analysis and DMS footprinting studies of the purine rich tract of the HER-2/neu promoter were indicative of a potassium dependent quadruplex. This quadruplex is formed by the GGA trinucleotide repeats with the sequence of GGAGGAG-GAGG (SEQ ID NO:2). Formulation of the quadruplex was abrogated by methylation of the N7 position of the guanines and was characterized by markedly hypersensitive adenines between protected guanines.

An NMR study of a GGA triplet repeat oligonucleotides published by Matsugami et al., supra, reported that oligonucleotides containing four GGA triplet repeats formed a quadruplex in the presence of potassium ions, which consisted of a guanine tetrad stacked onto a guanine-adenine heptad. The sequence of oligonucleotide having the quadruplex DNA structure was GGAGGAGGAGG (SEQ ID NO:2), which may be characterized by the motif (GGA)$_3$GG (SEQ ID NO:2). The position of the adenine bases in the heptad exposes the N3 position and likely accounts for their hypersensitivity to DMS. The structure on the bottom left indicates that two heptad/tetrad structures can stack onto one another to form a tetrad:heptad:heptad:tetrad dimer,and this stacking interaction of two intramolecular quadruplexes likely accounted for the slower mobility of the HER-2/nen promoter. The data are consistent with the formation of a heptad/tetrad quadruplex structure in the HER-2/neu promoter, and this structure represents a novel molecular target for the sequence selective recognition of genes containing this GGA repeat motif.

The c-MYB promoter also was studied with EMSA and DMS footprinting analysis. These studies indicated that two of the three regions of the c-MYB promoter containing the sequence GGAGGAGGAGG (SEQ ID NO:2) were capable of undergoing quadruplex formation, which are illustrated as regions I and II (see e.g., FIG. 2 for these regions). In contrast to the HER-2/neu promoter, the EMSA analysis did not demonstrate the presence of a slower migrating species in the presence of potassium. In the EMSA analysis, the lack of a band having altered mobility can be explained by dissociation during electrophoresis. The intramolecular stacking of two adjacent regions of heptad:tetrad formation in the c-MYB promoter could prevent the formation of intermolecular heptad/tetrad multimers, as seen in the HER-2/neu promoter EMSA.

Example 2

Determination that the Quadruplex Conformation is Biologically Significant

DNA polymerase arrest assays were performed on single stranded DNA templates representing the promoter regions of HER-2/neu and c-MYB oncogenes to establish the relative stability of the heptad:tetrad structures and their ability to arrest DNA polymerase activity. This assay clearly demonstrated a potassium-dependent arrest of taq DNA polymerase at the bases corresponding to the beginning of the heptad:tetrad structures in both the HER-2/neu and c-MYB promoters, implying that quadruplex formation prevents the translocation of the DNA polymerase through the DNA template.

In the DNA polymerase arrest assay, the purine rich strand of the HER-2/neu promoter was placed into an 86 nucleotide DNA template for primer extension by taq DNA polymerase. An example of the Taq polymerase stop assay used in the study is described in Han et al., *Nuci. Acids Res.* 27: 537-542 (1999), which is a modification of that used by Weitzmann et al., *J. Biol. Chem.* 271, 20958-20964 (1996). Briefly, a reaction mixture of template DNA (50 nM), Tris.HCl (50 mM), MgCl$_2$ (10 mM), DTT (0.5 mM), EDTA (0.1 mM), BSA (60 ng), and 5 '-end-labeled 18-mer template (~18 nM) was heated to 90° C. for 5 min and allowed to cool to ambient temperature over 30 min Taq Polymerase (1 µl) was added to the reaction mixture, and the reaction was maintained at a constant temperature for 30 minutes. Following the addition of 10 µl stop buffer (formamide [20 ml], 1 M NaOH [200 µl], 0.5 M EDTA [400 µl], 10 mg bromophenol blue), the reactions were separated on a preparative gel (12%) and visualized on a phosphorimager. Adenine sequencing was performed using double-stranded DNA Cycle Sequencing System from Life Technologies. The general sequence for the template strands was TCCAACTATGTATAC-INSERT-TTAGCGACACGCAATTGCTATAGTGAGTCGTATTA (SEQ ID NOS:27-28).

The DNA polymerase assay demonstrated the presence of a specific site of DNA polymerase arrest that occurred precisely at the beginning of the region that is involved in quadruplex formation. A guanine sequencing ladder created using dideoxy sequencing with the same primer and template is included adjacent to the polymerase arrest lanes to ascertain the precise location of the arrest. The polymerase arrest was dependent on the presence of potassium ions, further evidence that quadruplex formation was the type of secondary structure that creates the arrest. The polymerase arrest was relieved by increasing the temperature of the reaction, indicating that the quadruplex melted above a certain temperature. The HER-2/neu promoter quadruplex melted at 57° C.

Similarly, DNA polymerase arrested in the c-MYB promoter at two sites corresponding to the two quadruplex forming units closest to the primer. Again, polymerase arrest was potassium dependent, but in contrast to HER-2/neu, the quadruplex in c-MYB remained stable over the temperature gradient (37° to 57° C.) evaluated in this assay. Finally, a previously characterized quadruplex forming unit in the c-MYC promoter was included as a positive control, demonstrating potassium dependent DNA polymerase arrest in the NHE region of the c-MYC promoter.

In corroborating taq polymerase arrest assays, a gradient of potassium concentrations from 0 to 100 mM was used to confirm the dependence of the taq polymerase arrest on the presence of potassium in the DNA template. The sites of polymerase arrest are indicated, and their location at the beginning of the quadruplex forming units is confirmed by the guanine sequencing ladder.

Using c-MYB mutants that altered each of the three (GGA)$_4$ repeats individually, footprinting studies demonstrated that all three regions were capable of quadruplex formation and suggested that two of the three GGA triplet regions in the native c-MYB promoter interact to create a single tetrad:heptad:heptad:tetrad stack. c-MYB promoter mutations were introduced into each of the three quadruplex forming units individually as shown in FIG. 2 (a guanine was replaced with a cytosine at each of the positions indicated by larger text). A G to C mutation was introduced into each GG doublet in a given quadruplex forming unit, and the region I mutation is illustrated as an example.

A series of DMS footprinting reactions of the native and mutated c-MYB promoters indicated that each of the GGAG-GAGGAGG (SEQ ID NO:2) quadruplex forming units were capable of undergoing quadruplex formation, if the third quadruplex forming unit was mutated. The data suggested that each of the three individual units in the native c-MYB promoter underwent quadruplex formation, and the region II and III units were most favored at equilibrium and formed a tetrad:heptad:heptad:tetrad stack.

A luciferase promoter assay described in He T.-C. et al., *Science* 281: 1509-1512 (1998) also is utilized for the study of quadruplex formation. Specifically, a vector utilized for the assay is set forth in reference 11 of the He T.-C. et al. document. In this assay, HeLa S$_3$ cells are transfected using the Effectene lipid-based system (QLAgen) according to the manufacturer's protocol, using 0.1 µg of pRL-TK (Renilla luciferase reporter plasmid) and 0.9 µg of the Del-4 (wild-type) or mutated plasmids (see QIAgen Effectene Transfection Reagent Handbook, March 2001). Firefly and Renilla luciferase activities are assayed using the Dual Luciferase Reporter Assay System (Promega) in a 96-well plate format according to the manufacturer's protocol.

Example 3

Interaction of Compounds with Quadruplex DNA Structures in Vitro

Assays also provided evidence that certain binding agents, stabilized the quadruplexes formed by the HER-2/neu and c-MYB promoter sequences. A series of studies were performed using the DNA polymerase arrest assay to determine whether TMPyP4, telomestatin, and coralyne were capable of interacting with and stabilizing the heptad:tetrad structures formed in the c-MYB and HER-2/neu promoters. TMPyP4 is a porphyrin that was previously shown to interact with the quadruplex structure formed by the c-MYC promoter nuclease hypersensitivity element. Coralyne is a naphthylquinoline derivative and telomestatin is a ringed polypeptide.

The assays were performed over a temperature gradient of 37° C. to 57° C., and in the presence of potassium. The absence of a DNA binding drug showed the presence of a DNA polymerase arrest site that diminished with increasing temperature. In the presence of TMPyP4 over this temperature gradient, there was no apparent change in the stability of the HER-2/neu quadruplex. In contrast, in the presence of coralyne, there was a slight increase in the amount of DNA polymerase arrest observed at the highest temperature (57° C.) relative to the no drug control, showing that coralyne interacted with and stabilized the quadruplex structure. The data also showed that telomestatin interacted with and stabilized the HER-2/neu quadruplex with higher affinity than coralyne.

The DNA polymerase arrest assay was also performed with the c-MYB nucleic acid over a temperature gradient of 37° C. to 57° C. Surprisingly, in the minimal amount of potassium contributed by the taq polymerase enzyme suspension buffer, there was an apparent arrest site formed at the beginning of region I that was not previously observed in this DNA polymerase arrest assay in the absence of potassium (KCl minus lanes). In the presence of potassium but the absence of a DNA binding drug, the DNA polymerase arrested at regions II and III. Although the DNA polymerase arrest was slightly more prominent in the presence of the DNA binding drugs, it was necessary to further increase the temperature gradient to melt the DNA quadruplex and to better demonstrate stabilization of the quadruplex by the DNA binding drugs. The data demonstrated that TMPyP4, coralyne and telomestatin interacted with and stabilized the c-MYB nucleic acid. These data show that quadruplex forming sequences can be identified by detecting interaction and stabilization of a quadruplex structure by quadruplex interacting agents, and show that intramolecular heptad/tetrad monomers and dimers can be distinguished by detecting an interaction and stabilization with selective quadruplex interacting agents such as TMPyP4.

Example 4

Selective Recognition of Quadruplex Structures in Tumor Cells

Cells were treated with telomestatin (interacts with the putative tetrad:heptad in HER-2/neu) and TmPyP4 (negative control) at various concentrations and times. Cytotoxicity studies using MTS were performed to determine a non-toxic or minimally toxic dose and duration of treatment. Cells were harvested after treatment for RNA extraction, and "target" versus "non-target" gene expression is measured by real-time reverse-transcription PCR according to established methods.

Target genes included two known tetrad/heptad (T:H) forming genes, HER-2/neu and c-MYB. c-MYC was analyzed as a positive control, having a known chair quadruplex forming regulatory unit in the nuclease hypersensitive element of the P1 promoter. Non-target genes, beta-actin and GAPDH served as effective negative control genes for the differential effects of DNA interactive compounds on gene expression by stabilizing quadruplex DNA. TmPyP2 is a structural isomer of TmPyP4 that interacts only weakly with quadruplex DNA and was used as a negative control for demonstrating that the effects of cell treatment are due to TmPyP4 interaction with quadruplex DNA. Preliminary studies were conducted to evaluate a panel of cell lines from various model tumor types that contain high versus low level HER-2/neu expression (e.g., BT-474, SK-BR-3 versus MCF-7 breast cancer cells, HeLa cervical cancer cells).

The effects of cell treatment on c-MYB expression were compared to the effects of treatment on HER-2/neu expression, to evaluate the role of the T:H:H:T higher order structure in selective recognition by small molecules. Because adjacent (GGAGGAGGAGG) (SEQ ID NO:2) elements are capable of stacking to create a TmPyP4 binding site in vitro, it was expected that TmPyP4 suppress c-MYC but not HER-2/neu expression. While c-MYB is expressed in hematopoietic precursor cells and abnormal overexpression is generally related to hematopoietic malignancies, aberrant expression and even amplification of c-MYB is also seen in certain solid tumors, such as colon cancer and some breast cancers. Evolving evidence suggests a role for the expression of c-MYB in colon carcinogenesis. HER-2/neu also is expressed in some colon carcinomas and cell lines. Colo 205 is a colon cancer cell line that co-expresses HER-2/neu and c-MYB. Colo 205 cells are treated with telomestatin and TmPyP4 for analysis of changes in both HER-2/neu and c-MYB expression, using beta-actin and GAPDH as a control.

A panel of cell lines including SK-BR-3 breast cancer, BT-474 breast cancer, MCF-7 breast cancer, Colo-205 colon cancer, and HeLa cervical cancer were treated with the quadruplex interactive compound TmPyP4 to assess for the cytotoxicity of this agent against a panel of cell lines with various levels of expression of HER-2/neu, c-MYB, and c-MYC. At minimally cytotoxic doses, Colo-205 cells were analyzed for gene expression after treatment with TmPyP4 and using real-time reverse-transcription PCR. These studies showed a reduction in c-MYB and c-MYC RNA levels, but not a reduction in HER-2/neu, GAPDH, and B-actin levels, as predicted by the DNA polymerase arrest assays presented above. These findings demonstrate that a small molecule can distinguish between two DNA sequences, HER-2/neu and c-MYB, which have similar primary sequences but different secondary structures in tumor cells, and can selectively downregulate the expression of a target gene of interest on this basis. These data also provide preliminary reassurance that the cell free assay systems, such as the DNA polymerase arrest assay, can be used to predict the small molecule interaction with different target genes based on predicted DNA secondary structure formation in living cells.

Example 5

Regulation by Quadruplex Structures in Untranslated, Coding and Intronic Regions of Genes The polypurine tract of the c-MYB promoter is notable in that it is downstream of the transcription start site and located on the template strand. The c-MYB polypurine tract was inserted downstream of a T7 promoter, and it was shown in a polymerase arrest assay that secondary structure formation leads to arrest of nacent RNA transcripts at the precise sites predicted to form T:H DNA in a potassium dependent manner. Thus, the significance of the formation of this higher order DNA secondary structure is not isolated to the promoter or regulatory regions of genes, but can function to attenuate transcription in the untranslated, coding, or intronic regions of genes.

Each document cited is incorporated herein by reference in its entirety, including all figures, drawings, tables, text, and documents referenced therein.

What is claimed is:

1. A method for identifying a molecule that modulates the transcriptional activity of a native quadruplex DNA, which comprises
contacting a test quadruplex DNA with a candidate molecule, wherein the test quadruplex DNA comprises the nucleotide sequence AGAGAAGAGG(GGA)$_5$GAGGAGGAGGCGC (SEQ ID NO:16), and wherein G is guanine and A is adenine; and determining the presence or absence of an interaction between the candidate molecule and the test quadruplex DNA, whereby the candidate molecule that interacts with the test quadruplex DNA is identified as the molecule that modulates the transcriptional activity of the native quadruplex DNA.

2. The method of claim 1, wherein the test quadruplex DNA further comprises a nucleotide sequence comprising (GGA)$_4$AGA(GGA)$_3$GGC (SEQ ID NO:15); (GGA)$_4$ (SEQ ID NO:1); GGAGGGGGAGGGG (SEQ ID NO:17); AGGAGAA(GGA)$_2$GGT(GGA)$_3$G$_3$ (SEQ ID NO:18); (GGA)$_3$AGAATGCGA(GGA)$_2$G$_3$AGGAG (SEQ ID NO:19); CCGAA(GGA)$_2$A(GGA)$_3$G$_4$ (SEQ ID NO:20); (GGA)$_2$CCGA(GGA)$_2$ (SEQ ID NO:25); GGAA(GGA)$_3$ (SEQ ID NO:23); AGAAGAG(GGA)$_3$G (SEQ ID NO:22); AGCGA(GGA)$_8$GAGGAA (SEQ ID NO:21); or a combination thereof.

3. A method for identifying a nucleotide sequence capable of forming a quadruplex structure, which comprises contacting a cell with a quadruplex interacting agent, identifying a subset of RNA nucleotide sequences increased or decreased 2-fold or more in the cell as compared to a cell not contacted with the quadruplex interacting agent, and identifying a nucleotide sequence from the subset comprising AGAGAA- GAGG(GGA)$_5$GAGGAGGAGGCGC (SEQ ID NO:16) as the nucleotide sequence capable of forming a quadruplex structure.

4. A method for identifying the presence or absence of a quadruplex structure in a nucleic acid of a sample, comprising
   (a) providing a sample comprising a nucleic acid comprising AGAGAAGAGG(GGA)$_5$GAGGAGGAGGCGC (SEQ ID NO:16); and, a quadriplex-interacting agent, wherein the quadruplex-interacting agent binds to a quadruplex structure in a heptad/tetrad conformation;
   (b) contacting the sample with the quadruplex-interacting agent; and
   (c) detecting the presence or absence of an interaction between the nucleic acid quadruplex structure and the quadruplex-interacting agent, whereby the presence of an interaction is indicative the presence of the quadruplex structure in the nucleic acid.

5. A method for identifying a molecule that modulates transcription comprising
   (a) providing a quadruplex DNA; and, a candidate quadruplex DNA-binding molecule, wherein the quadruplex DNA comprises the nucleotide sequence AGAGAAGAGG(GGA)$_5$GAGGAGGAGGCGC (SEQ ID NO:16), and G is guanine and A is adenine, and the quadruplex DNA is in a heptad/tetrad conformation;
   (b) contacting the quadruplex DNA with the candidate quadruplex DNA-binding molecule, whereby the contacting occurs in a cell; and
   (c) determining the presence or absence of an interaction between the candidate quadruplex DNA-binding molecule and the quadruplex DNA, whereby the candidate molecule that interacts with the quadruplex DNA is identified as a molecule that modulates the transcription.

6. The method of claim 5, wherein the quadruplex DNA further comprises a nucleotide sequence comprising (GGA)$_4$AGA(GGA)$_3$GGC (SEQ ID NO:15); (GGA)$_4$ (SEQ ID NO:1); GGAGGGGGAGGGG (SEQ ID NO:17); AGGAGAA(GGA)$_2$GGT(GGA)$_3$G$_3$ (SEQ ID NO:18); (GGA)$_3$AGAATGCGA(GGA)$_2$G$_3$AGGAG (SEQ ID NO:19); CCGAA(GGA)$_2$A(GGA)$_3$G$_4$ (SEQ ID NO:20); (GGA)$_2$CCGA(GGA)$_2$ (SEQ ID NO:25); GGAA(GGA)$_3$ (SEQ ID NO:23);
AGAAGAG(GGA)$_3$G (SEQ ID NO:22); AGCGA(GGA)$_8$GAGGAA (SEQ ID NO:21); or a combination thereof.

* * * * *

UNITED STATES PATENT AND TRADEMARK OFFICE
CERTIFICATE OF CORRECTION

PATENT NO. : 7,405,041 B2  Page 1 of 1
APPLICATION NO. : 10/645471
DATED : July 29, 2008
INVENTOR(S) : Scot W. Ebbinghaus et al.

It is certified that error appears in the above-identified patent and that said Letters Patent is hereby corrected as shown below:

Col. 1, line 16, delete "CA 67760, CA 88310,"

Signed and Sealed this

Fourteenth Day of October, 2008

JON W. DUDAS
*Director of the United States Patent and Trademark Office*